US010745709B2

(12) United States Patent
McKinley et al.

(10) Patent No.: US 10,745,709 B2
(45) Date of Patent: Aug. 18, 2020

(54) GRASSES WITH ENHANCED STARCH CONTENT

(71) Applicant: The Texas A&M University System, College Station, TX (US)

(72) Inventors: Brian McKinley, College Station, TX (US); John E. Mullet, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/759,171

(22) PCT Filed: Sep. 14, 2016

(86) PCT No.: PCT/US2016/051733
§ 371 (c)(1),
(2) Date: Mar. 9, 2018

(87) PCT Pub. No.: WO2017/048840
PCT Pub. Date: Mar. 23, 2017

(65) Prior Publication Data
US 2019/0062770 A1    Feb. 28, 2019

Related U.S. Application Data

(60) Provisional application No. 62/218,372, filed on Sep. 14, 2015.

(51) Int. Cl.
*C12N 15/82* (2006.01)
*C12N 15/87* (2006.01)
*C12N 5/10* (2006.01)

(52) U.S. Cl.
CPC ........... *C12N 15/8245* (2013.01); *C12N 5/10* (2013.01); *C12N 15/8218* (2013.01); *C12N 15/8226* (2013.01); *C12N 15/87* (2013.01)

(58) Field of Classification Search
None
See application file for complete search history.

(56) References Cited

U.S. PATENT DOCUMENTS

2015/0203860 A1    7/2015    Lanahan

FOREIGN PATENT DOCUMENTS

| WO | 2009/149304 A2 | 12/2009 |
|---|---|---|
| WO | 2013/005152 A1 | 1/2013 |
| WO | 2014/164014 A1 | 10/2014 |
| WO | 2014/188428 A1 | 11/2014 |
| WO | 2015/054253 A1 | 4/2015 |

OTHER PUBLICATIONS

Dolferus et al 1994 Plant Physiology 105:1075-1087 (Year: 1994).*
Calvino, et al., "Characterization of the Small RNA Component of the Transcriptome From Grain and Sweet Sorghum Stems," BMC Genomics, 12:356 (2011).
Calvino, et al., "Screen of Genes Linked to High-Sugar Content in Stems by Comparative Genomics," Rice, 1(2):166-176 (2008).
Chuck, et al., "Overexpression of the Maize Corngrass1 MicroRNA Prevents Flowering, Improves Digestibility, and Increases Starch Content of Switchgrass," Proceedings of the National Academy of Sciences of the United States of America, 108(42):17550-17555 (2011).
Ermawar, et al., "Distribution, Structure and Biosynthetic Gene Families of (1,3;1,4)-β-glucan in Sorghum Bicolor," Journal of Integrated Plant Biology, 57(4):429-445, (2015).
Hirano, et al., "Survey of Genes Involved in Rice Secondary Cell Wall Formation Through a Co-expression Network," Plant and Cell Physiology, 54(11):1803-1821 (2013).
International Search Report for PCT/US16/51733, dated Feb. 6, 2017.
Jiang, et al., "Genetic Variation and Expression Diversity Between Grain and Sweet Sorghum Lines," BMC Genomics, 14:18 (2013).
Jung, et al., "Modifying Crops to Increase Cell Wall Digestibility," Plant Science, 185-186:65-77 (2012).
Martin, et al., "A Holistic High-throughput Screening Framework for Biofuel Feedstock Assessment That Characterizes Variations in Soluble Sugars and Cell Wall Composition in Sorghum bicolor," Biotechnology for Biofuels, 6:186 (2013).
McKinley, et al., "Dynamics of Biomass Partitioning, Stem Gene Expression, Cell Wall Biosynthesis, and Sucrose Accumulation During Development of Sorghum bicolor," The Plant Journal, 88(4):662-680 (2016).
Mitchell, et al., "A Novel Bioinformatics Approach Identifies Candidate Genes for the Synthesis and Feruloylation of Arabinoxylan," Plant Physiology, 144(1):43-53 (2007).
Murray, et al., "Sweet Sorghum Genetic Diversity and Association Mapping for Brix and Height," The Plant Genome-Abstract, 2(1):48-62 (2009).
Paterson, et al., "The Sorghum bicolor Genome and the Diversification of Grasses," Nature, 457(7229):551-556 (2009).

(Continued)

*Primary Examiner* — Brent T Page
(74) *Attorney, Agent, or Firm* — Dentons US LLP

(57) ABSTRACT

Methods and compositions for the production of monocot plants with increased starch content in stems are provided. In accordance with the invention, novel promoters and regulatory elements with specific temporal and spatial expression patterns are disclosed together with methods for the production of plants having desirable stem composition at harvest.

18 Claims, 2 Drawing Sheets
Specification includes a Sequence Listing.

(56) References Cited

OTHER PUBLICATIONS

Penning, et al., "Genetic Resources for Maize Cell Wall Biology," Plant Physiology, 151(4):1703-1728 (2009).
Qazi, et al., "Stem Sugar Accumulation in Sweet Sorghum—Activity and Expression of Sucrose Metabolizing Enzymes and Sucrose Transporters," Journal of Plant Physiology, 169(6):605-613 (2012).
Shen, et al., "A Genomics Approach to Deciphering Lignin Biosynthesis in Switchgrass." The Plant Cell, 25(11):4342-4361 (2013).
Taylor-Teeples, et al., "An Arabidopsis Gene Regulatory Network for Secondary Cell Wall Synthesis," Nature, 517(7536):571-575, (2015).
Wang, et al., "Genetic Diversity and Population Structure Analysis of Accessions in the US Historic Sweet Sorghum Collection," Theoretical and Applied Genetics, 120(1):13-23, (2009).
Weise, et al., "Engineering Starch Accumulation by Manipulation of Phosphate Metabolism of Starch," Plant Biotechnology Journal 10(5):545-554 (2012).
International Preliminary Report on Patentability for PCT/US16/51733, dated Mar. 29, 2018.

* cited by examiner

GRASSES WITH ENHANCED STARCH CONTENT

CROSS REFERENCE TO RELATED APPLICATIONS

This application is a 371 National Stage application of International Application No. PCT/US2016/051733, filed Sep. 14, 2016, which claims the benefit of U.S. Provisional Patent Application No. 62/218,372, filed Sep. 14, 2015, each of which are herein incorporated by reference in its entirety.

STATEMENT REGARDING FEDERALLY SPONSORED RESEARCH

This invention was made with partial government support by funding from the U.S. Department of Energy (DOE) under grant number 06-504416, 66780, and Great Lakes Bioenergy Research Center—U.S. Department of Energy (GLBRC-DOE) under grant number 06-504678, 66780. The government has certain rights in the invention.

INCORPORATION OF SEQUENCE LISTING

The sequence listing that is contained in the file named "TAMC034WO_ST25.txt," which is 77.8 kilobytes as measured in Microsoft Windows operating system and was created on Sep. 14, 2016, is filed electronically herewith and incorporated herein by reference.

FIELD OF THE INVENTION

The present invention relates to the field of agricultural biotechnology, and more specifically to compositions and methods for producing crops with high starch accumulation in stems at harvest.

BACKGROUND OF THE INVENTION

The stems of bioenergy sorghum and other C4 grasses represent more than 75% of plant shoot biomass when plants are harvested at the end of the season. The composition of stems affects the efficiency of conversion of stem biomass to biofuels, biopower, and its utility as a source of forage or feed for animals. Stem composition at harvest is therefore critically important for bioenergy crops. While grasses with various desirable properties have been selected, there remains a need in the art for producing varieties with improved starch accumulation in stems. Starch is a compact and energy dense polymer of hexose units derived from glucose, fructose and sucrose. Increased accumulation of starch in stems when stem sugar content reaches high levels could improve crop biomass yield by minimizing feedback inhibition of leaf photosynthesis and by increasing the capacity of stems to accumulate non structural carbohydrates (i.e., starch) and 'sink' strength. Efforts to identify sorghum lines exhibiting desirable stem composition have been complicated by the many factors which contribute to starch biosynthesis and breakdown, including the stage of plant development, signals from the photoperiod, temperature, and growing location. Without increased knowledge and availability of the regulatory elements driving expression of genes involved in starch biosynthesis or breakdown at various stages of plant development, it may not be practical to attempt to produce certain new genotypes of crop plants due to such challenges.

SUMMARY OF THE INVENTION

In one aspect, the present invention provides a DNA molecule comprising a DNA sequence selected from the group consisting of: a) a DNA sequence comprising a promoter region associated with a *Sorghum biocolor* gene selected from the group consisting of: a DNA sequence comprising a promoter region associated with a *Sorghum biocolor* gene selected from the group consisting of: Sobic.002G322000 Glucose-6-phosphate/Pi translocator, Sobic.002G075800 Seed Imbibition 2, Sobic.009G245000 AGPase Large subunit, Sobic.006G066800 Starch branching enzyme 2.2, Sobic.001G044800 Raffinose Synthase, Sobic.001G236400 UDP-Glycosyltransferase superfamily, Sobic.001G396400 bZIP Transcription Factor, Sobic.004G282900 Major Facilitator Superfamily, Sobic.010G047700 Starch synthase, Sobic.004G071200 UDP-Glycosyltransferase superfamily, Sobic.001G290400 NAC domain protein 71 NAM-2, Sobic.001G083900 Starch phosphorylase, Sobic.004G120100 Phosphoglucan water dikinase, Sobic.002G202700 WRKY76 expressed, Sobic.001G174100 GRAS family transcription factor, Sobic.001G396400 Basic region/leucine zipper 53 TF, Sobic.003G396600 ZOS5-12-C2H2 zinc finger TF, Sobic.009G180500 Myb-like HTH TF, Sobic.002G360100 ZOS3-12-C2H2 zinc finger TF, and Sobic.002G368700 OsMADS18 TF; b) a DNA sequence with at least 85 percent sequence identity to the DNA sequence of part (a); and c) a fragment of the DNA sequence of part (a) that has gene-regulatory activity; wherein said DNA sequence is operably linked to a heterologous transcribable polynucleotide molecule. In some embodiments, the present invention provides a DNA molecule comprising a DNA sequence selected from the group consisting of: a) a sequence selected from the group consisting of SEQ ID NOs:1-20; b) a sequence having at least 85 percent sequence identity to a sequence selected from the group consisting of SEQ ID NOs:1-20; and c) a fragment of any of SEQ ID NOs: 1-20 having gene-regulatory activity, wherein said DNA sequence is operably linked to a heterologous transcribable polynucleotide molecule. In certain embodiments, the DNA sequence has at least about 90 percent sequence identity or at least about 95 percent sequence identity to the DNA sequence of part (a). In further embodiments, the DNA sequence comprises gene-regulatory activity. In a certain embodiment, the DNA molecule comprises a DNA sequence comprising a sequence selected from the group consisting of SEQ ID NOs:1-20. In yet further embodiments, the heterologous transcribable polynucleotide molecule comprises a sequence encoding a protein involved in starch biosynthesis, for example an enzyme or transcription factor. In certain embodiments, the heterologous transcribable polynucleotide molecule in a plant suppresses expression of a target coding sequence, for example a protein involved in starch breakdown. In some embodiments, the protein involved in starch breakdown is selected from the group consisting of: glucan, water dikinase (GWD), β-amylase, and starch phosphorylase.

In another aspect, the invention provides a transgenic plant, plant part, cell, or seed comprising a DNA molecule of the invention. In some embodiments, the plant is a monocot, for example a C4 grass. In certain embodiments, the plant is a sorghum plant. In further embodiments, the invention provides a method of expressing a transcribable polynucleotide molecule comprising obtaining a transgenic plant according to the invention and cultivating plant, wherein the transcribable polynucleotide is expressed.

In yet another aspect, the invention provides a method of producing a transgenic plant with increased starch content in stems post-anthesis, comprising the steps of: a) transforming a plant cell with the DNA molecule of claim 1, wherein the heterologous transcribable polynucleotide molecule confers increased starch content when expressed in stems; b) regenerating a plant from the plant cell; and c) cultivating the regenerated plant. In some embodiments, the plant is a monocot, for example a C4 grass. In certain embodiments, the plant is a sorghum plant.

In a further aspect, the invention provides a method of producing a transgenic plant with increased starch content in stems in some instances post-anthesis, comprising the steps of: a) providing a plant cell; b) modifying the genome of the plant cell to alter a promoter sequence operably linked to a gene involved in starch breakdown or starch biosynthesis post-anthesis; c) regenerating a plant from the plant cell; and d) cultivating the regenerated plant. In some embodiments, step b) of modifying the genome of the plant cell comprises non-specific mutagenesis using for example, ethyl methanesulfonate (EMS) or X-ray mutagenesis, or targeted mutagenesis, using for example, zinc finger nucleases (ZFN), TALEN, or CRISPR technology.

DETAILED DESCRIPTION

Figure 1:
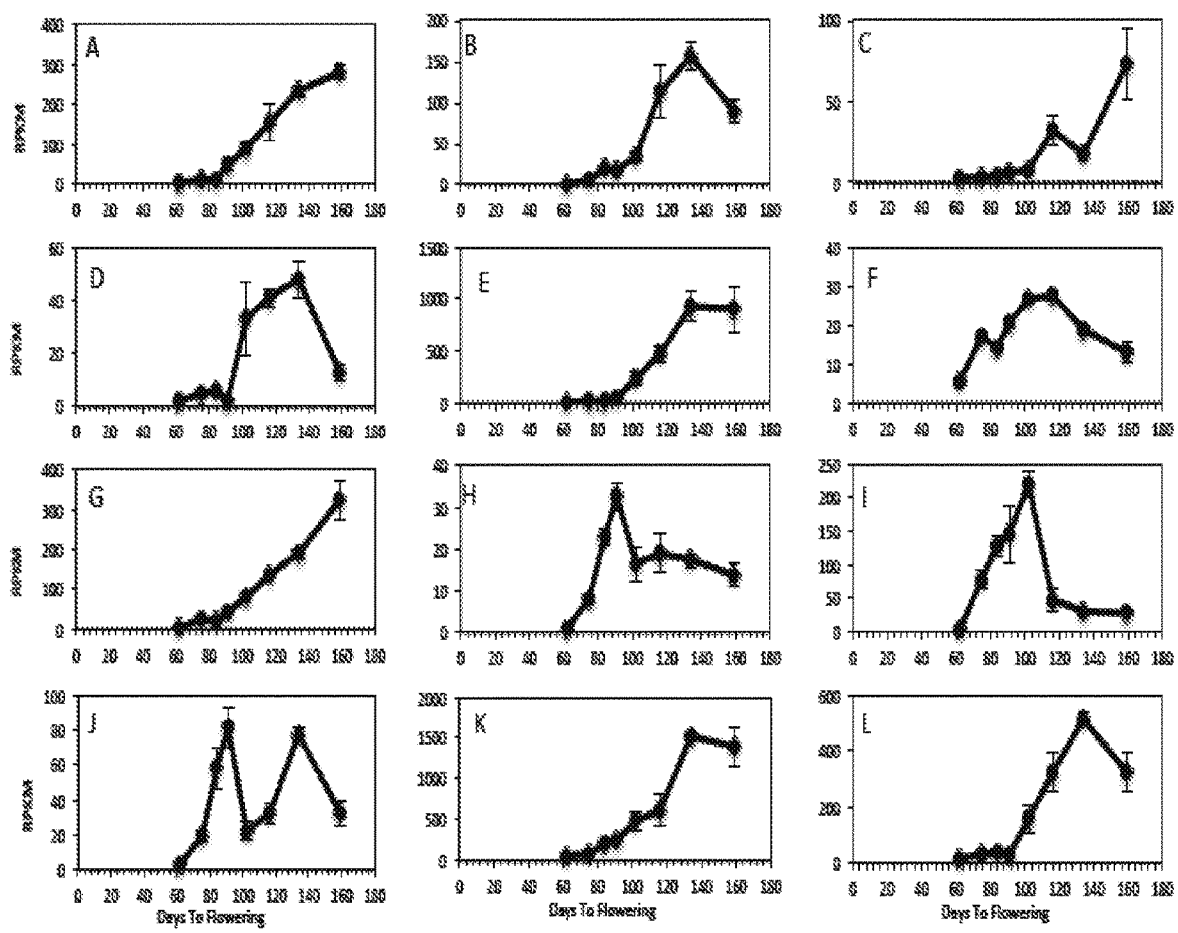
FIG. 1 shows expression profile of promoters selected for sorghum transformation, measured in Reads Per Kilobase of transcript per Million (RPKM) over 0 to 180 days to flowering. Promoter sequences are defined as 1-3 kbp regions upstream of the transcription start site for: (A) seed imbibition 2; (B) bZIP DNA binding Transcription Factor; (C) putative limonoid UDP-glucosyltransferase; (D) Alpha-glucan phosphorylase; (E) Raffinose Synthase Seed Imbibition Protein; (F) phosphoglucan, water dikinase; (G) UDP-Glucosyl Transferase; (H) WRKY 76 DNA Binding Transcription Factor; (I) Major Facilitator Superfamily with SPX (SYG1/Pho81/XRP1) domain-containing protein; (J) No Apical Meristem (NAM) protein; (K) similar to Glucose 6-Pi/Pi Transporter; and (L) Starch Branching Enzyme 2.2.

Sorghum and other C4 grasses are important crops for the production of biofuels, biopower, and for use as forage or feed for animals. The stems of bioenergy and some forage grasses represent more than 75% of plant shoot biomass when plants are harvested, and the stem's composition therefore represents a critically important trait in these plants. The composition of stems affects the efficiency of conversion of stem biomass to biofuels, biopower, and their utility for feeding animals. Stems of sorghum and sugarcane can accumulate high levels (~40% by weight) and concentrations (~0.5M) soluble sugars such as sucrose and glucose, however, starch accumulation in stems of these energy crops is low, usually <5% by weight.

Efforts to identify or produce sorghum lines with improved stem starch composition have previously been hindered by a limited understanding of the spatial and temporal regulation of genes controlling sorghum stem starch accumulation. This has been further complicated by a lack of information regarding the regulatory elements driving expression of these genes. Therefore, a need for bioenergy plants exhibiting optimal stem composition at harvest remains.

Despite the challenges associated with incomplete understanding of the regulation of stem composition, Applicants were able to identify regulatory elements useful in producing grasses that accumulate high levels of starch in their stems. For example, promoters driving expression of genes at low levels in stems prior to anthesis and at high levels post-anthesis are provided by the invention. Some of the regulatory elements/promoters are derived from genes expressed at low levels in stems until just before grain maturity, and then they increase gene expression to high levels in stems at grain maturity and for weeks after grain is mature. These newly identified gene regulatory elements/promoters allow for the design of grasses with improved accumulation of starch in their stems for use in biofuel and biopower applications, or as forage or feed for animals. The regulatory elements that selectively induce gene expression at and post-grain maturity are particularly useful for modifying stem composition without affecting grain yield.

In some embodiments, the invention provides promoters and regulatory elements that regulate expression of an operably linked coding sequence at low levels in stems prior to anthesis and at high levels post-anthesis or post-grain maturity. The invention further provides DNA constructs comprising these promoters and regulatory elements operably linked to transcribable polynucleotide molecules encoding proteins involved in starch biosynthesis. DNA constructs for suppressing expression of genes encoding proteins involved in starch breakdown through RNAi pathways are further provided utilizing the promoter and regulatory sequences of the present invention.

In further embodiments, the invention provides methods of designing and producing transgenic bioenergy plants with increased starch content in stems post-anthesis, which have increased utility for biofuel or animal feed applications. In some embodiments, transgenic plants are produced by transforming a plant cell with a DNA construct comprising a novel promoter or regulatory element of the invention operably linked with a heterologous sequence capable of modifying starch biosynthesis or breakdown. In other embodiments, the invention provides methods of designing plants with increased starch content in stems post-anthesis, or post-grain maturity, by modifying the genome of a plant cell to alter one of the promoter or regulatory sequences identified by the invention, thereby modifying the expression of an associated gene involved in starch breakdown or biosynthesis. Genome modification can be accomplished through non-specific or targeted mutagenesis as described herein.

The regulatory sequences and methods provided by the invention therefore enable the production of bioenergy plants exhibiting optimal stem compositions at harvest. These novel plants fulfill the need for improved sources of biomass for use in biofuel, biopower, and forage applications.

II. Bioenergy Crops

The composition of the stems of bioenergy sorghum and other C4 grasses is an important factor in the efficiency of conversion of stem biomass to biofuels, biopower, and their utility as forage or feed for animals. Bioenergy crops that accumulate high levels of starch in stems post-anthesis have a number of advantageous properties. For example, these crops produce biomass that has higher conversion efficiency (due to increased amounts of amylose or starch content), greater stability, and improved storage properties. Crops accumulating high levels of starch in stems post-anthesis also produce a higher biomass yield than plants with lower levels of starch in stems.

An important constraint and cost in the production of biofuels is the difficulty of converting plant biomass to sugars. The sugars released from biomass are fed to microbes for production of ROH-biofuels (i.e., ethanol, butanol), fatty acids (for biodiesel), and other biomolecules. The bioenergy plants with high starch content provided by the invention overcome previous limitations in conversion efficiency because starch can be easily converted to sugars using amylase for microbial production of biofuels, bioproducts or used as forage.

Bioenergy crops which accumulate higher levels of starch also produce biomass which has greater stability and improved storage properties. Sugarcane and sweet sorghum accumulate high levels of sucrose (up to 40% by weight) in their stems before harvest. The sucrose is of high value and readily converted to ethanol. However, because sucrose is soluble, a plant can only accumulate approximately 25% of its fresh weight as sucrose. Once these plants are harvested, the sucrose must be extracted rapidly in order to prevent microbial degradation. Production of energy grass crops that divert some or most of the sugars/sucrose in stems to starch will provide a higher density, more stable biomass feedstock compared to prior versions of sugarcane or sweet sorghum. A feedstock with high starch content will increase production efficiency by enabling mills to store biomass similar to grain, prior to utilization of biomass for biofuels production.

The bioenergy grasses of the present invention engineered to accumulate starch post-grain maturity further produce higher biomass yield. This may be due in part to extended biomass accumulation resulting from the creation of a strong sink for sugars in stems. The creation of a larger sink for sugars produced by photosynthesis in stems functions post-grain maturity to keep sucrose and glucose levels low in leaves and stems, reducing sugar induced inhibition of photosynthesis (and leaf senescence) to enhance forage quality. In addition, low sucrose levels in stems repress tillering at grain maturity increasing the stability of sugars and starch accumulated in stems that would otherwise be mobilized to support growth of tillers. The promoters and regulatory elements provided by the present invention can further be used to produce non-flowering dedicated bioenergy grasses that accumulate high levels of starch.

The present invention provides promoters and regulatory elements that enable the design of grass stems with improved composition. The endogenous genes regulated by these promoters are expressed at low levels in stems prior to anthesis and at 10-fold to more than 50-fold higher levels post-anthesis. In some embodiments, expression driven by the promoters identified by the invention peaks approximately at or just after grain maturity, with expression remaining elevated post-grain maturity in stems thereby extending the duration of biomass accumulation.

Methods for designing grasses that accumulate starch in their stems utilizing these unique promoters are further provided. In some embodiments, the promoters of the present invention are operably linked to a heterologous sequence capable of suppressing expression of a target gene through RNAi pathways. In certain embodiments, the invention provides constructs for the RNAi suppression of genes encoding enzymes involved in starch breakdown, for example glucan, water dikinase (GWD), β-amylase, and starch phosphorylase, in order to produce plants that accumulate high amounts of starch in stems post-anthesis. Further embodiments of the invention modify the elements of newly identified regulatory modules required for induction of the genes for starch breakdown in stems post-anthesis using genome editing (i.e., TALEN, CRISPR/Cas), reducing their expression in stems. Methods for deploying transgenic plants, including sorghum and other C4 grasses, engineered to accumulate starch in their stems as inbreds, hybrids and wide-hybrids are further provided.

The methods of the present invention can be used to produce transgenic plants which accumulate high amounts of starch in stems post-anthesis thereby enhancing yield, biomass stability, conversion efficiency to biofuels, and the value of the resulting crops for production of bioenergy, bioproducts, and forage. In certain embodiments, the transgenic or genome edited plants of the present invention are monocot plants, including, but not limited to sorghum, maize, miscanthus, cane, and switchgrass.

III. DNA Molecules

As used herein, the term "DNA" or "DNA molecule" refers to a double-stranded DNA molecule of genomic or synthetic origin, i.e., a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein is that required by Title 37 of the United States Code of Federal Regulations § 1.822 and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native state. In one embodiment, the term "isolated" is also used herein in reference to a DNA molecule that is at least partially separated from nucleic acids which normally flank the DNA molecule in its native state. Thus, DNA molecules fused to regulatory or coding sequences with which they are not normally associated, for example as the result of recombinant techniques or genome modification, are considered isolated herein. Such molecules are considered isolated even when present, for example in the chromosome of a host cell, or in a nucleic acid solution. The term "isolated" as used herein is intended to encompass molecules not present in their native state.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein "sequence identity" refers to the extent to which two optimally aligned polynucleotide or polypeptide sequences are identical throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *Journal of Molecular Biology*, 48:443-453 (1970)) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Advances in Applied Mathematics*, 2:482-489, 1981, Smith et al., *Nucleic Acids Research*, 11:2205-2220 (1983)). The percent identity is most preferably determined using the "Best Fit" program.

Useful methods known to those of skill in the art for determining sequence identity are also disclosed in *Guide to Huge Computers*, Martin J. Bishop, ed., Academic Press, San Diego (1994) and Carillo, H., and Lipton, D., *Applied Math.*, 48:1073 (1988). More particularly, preferred computer programs for determining sequence identity include the Basic Local Alignment Search Tool (BLAST) programs, which are publicly available from National Center Biotechnology Information (NCBI) at the National Library of Medicine, National Institute of Health, Bethesda, Md. 20894 (see also, *BLAST Manual*, Altschul et al., NCBI, NLM, NIH and Altschul et al., *Journal of Molecular Biology*, 215:403-410 (1990)). For polynucleotide sequence BLASTN can be used to determine sequence identity, and version 2.0 or higher of BLAST programs allows the introduction of gaps (deletions and insertions) into alignments. In certain aspects, a DNA molecule of the invention is at least about 70, 75, 80, 85, 90, 91, 92, 93, 94, 95, 96, 97, 98, 99 or 99.5 percent identical to a polynucleotide sequence of the present invention. Thus, one embodiment of the invention is a DNA molecule that has at least about 98% sequence identity with a polynucleotide sequence provided by the present invention.

IV. Promoters

As used herein, the term "promoter" refers generally to a DNA molecule that is involved in recognition and binding of RNA polymerase II and other proteins (trans-acting transcription factors) to initiate or regulate transcription. "Promoter activity" refers to the ability to initiate, increase, or affect transcription of an operably linked transcribable DNA molecule. A promoter may be initially isolated from the 5' untranslated region (5' UTR) of a genomic copy of a gene or from the genomic sequence immediately upstream of the transcription start site of a gene. Alternately, promoters may be synthetically produced or manipulated DNA molecules. Promoters may also be chimeric, that is a promoter produced through the fusion of two or more DNA molecules. In certain embodiments of the invention, promoters of the invention include a promoter region associated with a *Sorghum biocolor* gene selected from the group consisting of: Sobic.002G322000 Glucose-6-phosphate/Pi translocator, Sobic.002G075800 Seed Imbibition 2, Sobic.009G245000 AGPase Large subunit, Sobic.006G066800 Starch branching enzyme 2.2, Sobic.001G044800 Raffinose S ynthase, Sobic.001G236400 UDP-Glycosyltransferase superfamily, Sobic.001G396400 bZIP Transcription Factor, Sobic.004G282900 Major Facilitator Superfamily, Sobic.010G047700 Starch synthase, Sobic.004G071200 UDP-Glycosyltransferase superfamily, Sobic.001G290400 NAC domain protein 71 NAM-2, Sobic.001G083900 Starch phosphorylase, Sobic.004G120100 Phosphoglucan water dikinase, Sobic.002G202700 WRKY76 expressed, Sobic.001G174100 GRAS family transcription factor, Sobic.001G396400 Basic region/leucine zipper 53 TF, Sobic.003G396600 ZOS5-12-C2H2 zinc finger TF, Sobic.009G180500 Myb-like HTH TF, Sobic.002G360100 ZOS3-12-C2H2 zinc finger TF, and Sobic.002G368700 OsMADS18 TF, or variants or fragments thereof. In some embodiments, promoters of the invention comprise SEQ ID NOs:1-20, or variants or fragments thereof.

Promoters may be characterized by their gene expression pattern, i.e., as constitutive and/or by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable DNA molecule.

As used herein, a "gene expression pattern" is any pattern of gene expression. The term "gene expression" refers to the transcription of a transcribable DNA molecule into a transcribed RNA molecule. Gene expression may be characterized by its temporal, spatial, developmental, tissue, environmental, physiological, pathological, cell cycle, and/or chemically responsive qualities as well as by quantitative or qualitative indications. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" refers to the translation of a transcribed RNA molecule into a protein molecule. Protein expression may be characterized by its temporal, spatial, developmental, or morphological qualities as well as by quantitative or qualitative indications.

As used herein, the term "gene-regulatory activity" refers to the ability to affect the expression pattern of an operably linked transcribable DNA molecule by affecting the transcription and/or translation of that DNA molecule. Gene-regulatory activity may be positive and/or negative and the effect may be characterized by its temporal, spatial, developmental, tissue, environmental, physiological, pathological, cell cycle, and/or chemically responsive qualities as well as by quantitative or qualitative indications.

As used herein, the term "regulatory element" refers to a DNA molecule having gene-regulatory activity, i.e., one that has the ability to affect the transcription, RNA processing, translation or stability of an operably linked transcribable DNA molecule. Regulatory elements such as promoters, leaders, introns, and transcription termination regions are DNA molecules that have gene-regulatory activity and play an integral part in the overall expression of genes in living cells. Isolated regulatory elements, such as promoters, that function in plants are therefore useful for modifying plant phenotypes through the methods of genetic engineering.

A promoter may comprise fragments that have independent promoter activity. Promoter fragments may be useful alone or in combination with other promoters and promoter fragments, such as in constructing chimeric promoters. Fragments of a promoter comprise at least about 50, 95, 150, 250, 500, and 750 contiguous nucleotides of the DNA sequence of the promoter molecule. In certain embodiments of the invention, promoters of the invention include fragments the promoter sequences provided by the invention comprising at least about 50, 95, 150, 250, 500, 750, 1000, or 1500 contiguous nucleotides of the promoter sequences provided by the invention, and having gene-regulatory activity.

A promoter or promoter fragment may also be analyzed for the presence of known promoter elements, i.e., DNA sequence characteristics, such as a TATA-box and other known transcription factor binding site motifs. Identification of such known promoter elements may be used by one of skill in the art to design modified versions of the promoter having a similar expression pattern to the original promoter. Such modified versions of the promoter may be a shorter or truncated version of the original promoter and/or a variant version of the sequence of the original promoter, such as one with different restriction enzyme sites, internal deletions, and/or internal insertions. Such modified versions would usually have the same or similar expression pattern of the original promoter. Production of modified versions of the chimeric promoters of the present invention is well within the ordinary skill of the art and is encompassed within the scope of the present invention.

The invention disclosed herein provides novel promoters and regulatory elements. The design, construction, and use of these DNA molecules are objects of this invention. The invention also includes DNA constructs comprising the promoters; transgenic plant cells, plants, and seeds comprising the chimeric promoters operably linked to a transcribable DNA molecule; and methods of making and using the chimeric promoters, the DNA constructs comprising the chimeric promoters, and the transgenic plant cells, plants, and seeds comprising the chimeric promoters. In further embodiments, the invention provides plant cells, plants, and seeds with modified genomes which result in enhanced potential for starch accumulation.

V. Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e., operably linked. As used herein, the term "vector" means any recombinant polynucleotide construct that may be used for the purpose of transformation, i.e., the introduction of heterologous DNA into a host cell.

As used herein, the term "operably linked" refers to a first molecule joined to a second molecule, wherein the molecules are so arranged that the first molecule affects the function of the second molecule. The two molecules may be part of a single contiguous molecule and may be adjacent. For example, a promoter is operably linked to a transcribable DNA molecule if the promoter modulates transcription of the transcribable DNA molecule of interest in a cell.

Methods are known in the art for assembling and introducing constructs into a cell in such a manner that the transcribable DNA molecule is transcribed into a functional mRNA molecule that is translated and expressed as a protein product. For the practice of the present invention, conventional compositions and methods for preparing and using constructs and host cells are well known to one skilled in the art, see, for example, *Molecular Cloning: A Laboratory Manual*, $3^{rd}$ edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011, all of which are hereby incorporated by reference in their entirety. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology*, 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA,* 82: 5824-5828 (1985)).

Various regulatory elements may be included in a construct. Any such regulatory elements may be provided in combination with other regulatory elements. Such combinations can be designed or modified to produce desirable regulatory features. Constructs of the present invention would typically comprise one or more regulatory elements operably linked to a transcribable DNA molecule operably linked to a 3' transcription termination molecule.

As used herein, the term "leader" refers to a DNA molecule isolated from the untranslated 5' region (5' UTR) of a genomic copy of a gene and defined generally as a segment between the transcription start site (TSS) and the coding sequence start site. Alternately, leaders may be synthetically produced or manipulated DNA elements. A leader can be used as a 5' regulatory element for modulating expression of an operably linked transcribable DNA molecule. For example, non-translated 5' leaders derived from heat shock protein genes have been demonstrated to enhance gene expression in plants (see, for example, U.S. Pat. Nos. 5,659,122 and 5,362,865, all of which are hereby incorporated by reference). Promoter molecules of the present invention may optionally comprise a native leader linked to the plant promoter segment for which it is naturally found. This molecule may be replaced with a heterologous leader.

As used herein, the term "intron" refers to a DNA molecule that may be isolated or identified from the genomic copy of a gene and may be defined generally as a region spliced out during mRNA processing prior to translation. Alternately, introns may be synthetically produced or manipulated DNA elements. Introns may themselves contain elements such as cis-elements or enhancer elements that effect the transcription of operably linked genes. An intron may be used as a regulatory element for modulating expression of an operably linked transcribable DNA molecule. A construct may comprise introns. The introns may or may not be heterologous with respect to the transcribable DNA molecule sequence. The transcribable DNA molecule sequence in the recombinant vector may comprise introns. The introns may be heterologous with respect to the transcribable DNA molecule sequence. Examples of introns include the rice actin intron (U.S. Pat. No. 5,641,876, hereby incorporated by reference) and the corn HSP70 intron (U.S. Pat. No. 5,859,347, hereby incorporated by reference).

As used herein, the term "3' transcription termination molecule" or "3' region" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. "polyA tail." A 3' transcription termination molecule may be operably linked to and located downstream of a transcribable DNA molecule. A 3' transcription termination molecule may include polynucleotides that provide a polyadenylation signal and other regulatory signals capable of affecting transcription, mRNA processing or gene expression. PolyA tails are thought to function in mRNA stability and in initiation of translation. Examples of 3' transcription termination molecules are the nopaline synthase 3' region (nos 3') (see, Fraley, et al., *Proc. Natl. Acad. Sci. USA*, 80: 4803-4807 (1983)), wheat hsp17 3' region (T-Ta.Hsp17), pea rubisco small subunit 3' region (T-Ps.RbcS2:E9), cotton E6 3' region (U.S. Pat. No. 6,096,950, hereby incorporated by reference), 3' regions disclosed in WO0011200A2, hereby incorporated by reference), and other 3' regions known in the art that can be used in combination with a transcribable DNA molecule, such as the coixin terminator (U.S. Pat. No. 6,635,806, hereby incorporated by reference).

VI. Transcribable DNA Molecules

As used herein, the term "transcribable DNA molecule" refers to any DNA molecule capable of being transcribed into a RNA molecule, including, but not limited to, those having protein coding sequences and sequences useful for gene suppression. A "transgene" comprises a transcribable DNA molecule heterologous to a host cell.

A promoter of the present invention may be operably linked to a transcribable DNA molecule that is heterologous with respect to the promoter molecule. The term "heterologous" refers to the relationship between two or more polynucleotide molecules that are derived from different sources. For example, a promoter is heterologous with respect to a transcribable DNA molecule if such a combination is not normally found in nature. In addition, a particular molecule may be "heterologous" with respect to the cell or organism into which it is inserted (i.e., does not naturally occur in that particular cell or organism).

The transcribable DNA molecule may generally be any DNA molecule for which expression of an RNA transcript is desired. Such expression of an RNA transcript may result in translation of the resulting mRNA molecule and thus protein expression. Alternatively, a transcribable DNA molecule may be designed to ultimately cause decreased expression of a specific gene or protein. This may be accomplished by using a transcribable DNA molecule that is oriented in the antisense direction. One of ordinary skill in the art is familiar with using such antisense technology. Briefly, as the antisense transcribable DNA molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a chimeric promoter of the present invention, operably linked to a transcribable DNA molecule so as to modulate transcription of the transcribable DNA molecule at a desired level or in a desired pattern upon introduction of said construct into a plant cell. In one embodiment, the transcribable DNA molecule comprises a protein-coding region of a gene, and the chimeric promoter affects the transcription of an RNA molecule that is translated and expressed as a protein product. In another embodiment, the transcribable DNA molecule comprises an antisense region of a gene, and the chimeric promoter affects the transcription of an antisense RNA molecule or other similar inhibitory RNA molecule (i.e., dsRNA mediating RNAi) in order to inhibit expression of a specific RNA molecule of interest in a target host cell.

A DNA construct of the present invention may further comprise a selectable marker. As used herein the term "marker" refers to any transcribable DNA molecule whose expression, or lack thereof, can be screened for or scored in some way. Marker genes for use in the practice of the present invention include, but are not limited to transcribable DNA molecules encoding β-glucuronidase (GUS described in U.S. Pat. No. 5,599,670, which is hereby incorporated by reference), green fluorescent protein and variants thereof (GFP described in U.S. Pat. Nos. 5,491,084 and 6,146,826, both of which are hereby incorporated by reference), proteins that confer antibiotic resistance, or proteins that confer herbicide tolerance.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art.

VII. Cell Transformation

The invention further provides methods of producing transformed cells and plants which comprise a promoters or DNA constructs of the present invention. The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing heterologous polynucleic acid molecules into plant cells. The method generally comprises the steps of selecting a suitable host cell, transforming the host cell with a recombinant vector, and obtaining the transformed host cell. Suitable methods include bacterial infection (e.g., *Agrobacterium*), binary bacterial artificial chromosome vectors, direct delivery of DNA (e.g., via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.,* 42: 205 (1991)).

Any of the above described methods may be utilized to transform a host cell with one or more promoters, regulatory elements, or constructs of the present invention. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Methods for transforming dicotyledonous plants, primarily by use of *Agrobacterium tumefaciens* and obtaining transgenic plants have been published for cotton (U.S. Pat. Nos. 5,004,863; 5,159,135; and 5,518,908); soybean (U.S. Pat. Nos. 5,569,834 and 5,416,011; see also, McCabe, et al., *Biotechnolgy,* 6:923 (1988) and Christou et al., *Plant Physiol.* 87:671-674 (1988)); *Brassica* (U.S. Pat. No. 5,463,174); peanut (Cheng et al., *Plant Cell Rep.,* 15:653-657 (1996) and McKently et al., *Plant Cell Rep.,* 14:699-703 (1995)); papaya; and pea (Grant et al., *Plant Cell Rep.,* 15:254-258 (1995)).

Transformations of monocotyledon plants using electroporation, particle bombardment, and *Agrobacterium* have also been reported. Transformation and plant regeneration have been achieved in asparagus (Bytebier, et al., *Proc. Natl. Acad. Sci.* (*USA*), 84:5354 (1987)); barley (Wan and Lemaux, *Plant Physiol,* 104:37 (1994)); maize (Rhodes, et al., *Science* 240:204 (1988), Gordon-Kamm, et al., *Plant Cell,* 2:603-618 (1990), Fromm, et al., *Bio/Technology,* 8:833 (1990), Koziel et al., *Bio/Technology,* 11:194 (1993), and Armstrong, et al., *Crop Science,* 35:550-557 (1995)); oat (Somers, et al., *Bio/Technology,* 10:1589 (1992)); orchard grass (Horn, et al., *Plant Cell Rep.* 7:469 (1988)); rye (De la Pena, et al., *Nature,* 325:274 (1987)); sugarcane (Bower and Birch, *Plant Journal,* 2:409 (1992)); sorghum (Casas, et al., *Proc. Natl. Acad. Sci.* (*USA*), 1:90(23) (1993)); tall fescue (Wang, et al., *Bio/Technology,* 10:691 (1992)); and wheat (Vasil, et al., *Bio/Technology,* 10:667 (1992) and U.S. Pat. No. 5,631,152).

The regeneration, development, and cultivation of plants from transformed plant protoplast or explants is well known in the art (see, for example, Weissbach and Weissbach, *Methods for Plant Molecular Biology*, (Eds.), Academic Press, Inc., San Diego, Calif. (1988) and Horsch et al., *Science,* 227:1229-1231 (1985)). Transformed cells are generally cultured in the presence of a selective media, which selects for the successfully transformed cells and induces the regeneration of plant shoots and roots into intact plants (Fraley, et al., *Proc. Natl. Acad. Sci. U.S.A.,* 80: 4803 (1983)). Transformed plants are typically obtained within two to four months.

The regenerated transgenic plants are self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of California, Davis, Calif., 50-98 (1960); Simmonds, *Principles of crop improvement*, Longman, Inc., New York, 369-399 (1979); Sneep and Hendriksen, Plant breeding perspectives, Wageningen (ed), Center for Agricultural Publishing and Documentation (1979); Fehr, *Soybeans: Improvement, Production and Uses,* 2nd Edition, Monograph., 16:249 (1987); Fehr, *Principles of variety development, Theory and Technique*, (Vol 1) and *Crop Species Soybean* (Vol 2), Iowa State Univ., Macmillian Pub. Co., NY, 360-376 (1987). Conversely, pollen from non-transgenic plants may be used to pollinate the regenerated transgenic plants.

Transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used trans gene expression.

The seeds of the plants of the invention can be harvested from fertile transgenic plants and be used to grow progeny generations of transformed plants of this invention including hybrid plant lines comprising the construct of the invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleic acid molecule to its progeny. Progeny includes any regenerable plant part or seed comprising the transgene derived from an ancestor plant. The transgenic plant is preferably homozygous for the transformed polynucleic acid molecule and transmits that sequence to all of it's offspring upon as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

VIII. Gene Suppression

As used herein the terms "gene suppression" and "suppression of a target coding sequence" are intended to refer to any of the well-known methods for reducing the levels of protein produced as a result of gene transcription to messenger RNA (mRNA) and subsequent translation of the mRNA. Gene suppression is also intended to mean the reduction of protein expression from a gene or a coding sequence including posttranscriptional gene suppression and transcriptional suppression. Posttranscriptional gene suppression is mediated by the homology between of all or a part of a mRNA transcribed from a gene or coding sequence targeted for suppression and the corresponding double stranded RNA (dsRNA), small interfering RNA (siRNA) or microRNA (miRNA) used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi). Transcriptional suppression is mediated by the presence in the cell of a gene suppression agent, such as dsRNA, siRNA or miRNA, exhibiting substantial sequence identity to a portion of the target sequence or the complement thereof. Gene suppression may be effective against a native plant gene associated with a trait, e.g., to provide plants with reduced levels of a protein encoded by the native gene or with enhanced or reduced levels of an affected metabolite. Gene suppression can also be effective against heterologous target genes that are stably transformed into the plant genome.

The use of dsRNA to suppress genes in plants is disclosed in WO 99/53050, WO 99/49029, U.S. Patent Application Publication No. 2003/0175965 A1, and 2003/0061626 A1, U.S. patent application Ser. No. 10/465,800, and U.S. Pat. Nos. 6,506,559, and 6,326,193. Techniques for RNAi are well known in the art and are described in, for example, Lehner et al., (2004) and Downward (2004).

RNAi methodology takes advantage of the fact that nucleic acids tend to pair with "complementary" sequences. Such complementarity may not be perfect, allowing for incomplete base-pairing or mismatching to regulate the expression of several sequences with similar but not identical sequences. dsRNA, siRNA, or miRNA, when expressed or introduced into a target cell, can specifically bind to their target polynucleotide and interfere with transcription, RNA processing, transport, translation and/or stability. RNAi constructs, or DNA encoding such RNA's, may be employed to inhibit gene transcription or translation or both within a host cell, either in vitro or in vivo, such as within a host plant cell.

Inhibition of target gene expression may be quantified by measuring either the produced target RNA or the protein produced by translation of the target RNA and the consequences of inhibition can be confirmed by examination of the outward properties of the cell or organism. Techniques for quantifying RNA and proteins are well known to one of ordinary skill in the art.

IX. Genome Modification

In some embodiments, the genome of a cell is modified such that a promoter or regulatory element provided by the invention is altered to increase or decrease expression of a gene involved in starch breakdown or starch biosynthesis. The modification of the genome may comprise non-specific or targeted mutagenesis.

Methods of genome modification are well-known in the art. Methods of non-specific genome modification include any methods known in the art for making changes to a genome of a cell, such as using radiation or chemical agents. Examples of non-specific mutagenesis include ethyl methanesulfonate (EMS) or X-ray mutagenesis.

Methods for site-specific or targeted genome modifications are also well-known in the art, and include any methods for making specific and intentional changes to the DNA sequence of a genome, include a promoter region, gene-regulatory region, or coding region of the genome. Examples of site-specific genome modification include the use of zinc finger nucleases (ZFN), TALEN technology, or CRISPR/Cas technology (described in, e.g. US 2013/0326645, WO 2013/188522, WO 2013/191769, incorporated herein by reference) to alter the specific promoter or regulatory sequences identified by the present invention.

In one exemplary embodiment, site-specific genome modification can be accomplished by using a guide nucleic acid, such as a guide RNA (gRNA) molecule, to target a nuclease to a region of a genome corresponding to a promoter or regulatory element provided by the invention to disrupt that region of the genome in a plant cell. A modification based on a donor DNA template can then be introduced within that genomic region using various genome-editing methods. A plant regenerated from a modified plant cell comprises a modified genome, and may exhibit a modified phenotype or other property depending on the genetic region that has been altered. In certain embodiments, sequences comprising the promoter regions of the invention can be targeted for modification using genome-editing techniques, enabling the creation of improved mutants or transgenic lines.

X. Methods for Producing Plants with Increased Starch Accumulation in Stems

The invention further provides methods for producing plant lines exhibiting increased starch accumulation in stems by breeding plants comprising the DNA constructs of the present invention. In some embodiments, a first plant or germplasm (the donor) can be crossed with a second plant or germplasm (the recipient) to create an introgressed plant or germplasm as part of a breeding program designed to confer desired starch accumulation traits to the recipient plant or germplasm. In some aspects, one or more transgenes can be conferred to the recipient. These breeding methods can be carried out in any bioenergy crop plant, including C4 grasses such as sorghum, maize, miscanthus, cane, and switchgrass.

The introgression of one or more desired genetic loci or transgenes from a donor line into another is achieved via a cross followed by selfing or one or more backcrosses to a recurrent parent accompanied by selection to retain one or more genetic elements related to starch accumulation from the donor parent. Markers associated with starch accumulation may be assayed in progeny and those progeny with one or more favorable markers selected for advancement. In another aspect, one or more markers can be assayed in the progeny to select for plants with the genotype of the agronomically elite parent. It is expected that trait introgression activities may require more than one generation, wherein progeny are crossed to the recurrent (agronomically elite) parent or selfed.

In some embodiments, plants engineered according to the present invention to accumulate compounds useful for biofuels production or for forage or feed are crossed to elite R-lines (pollenators) or A/B-lines (seed parents) for hybrid plant production. Plants useful in this method include any bioenergy crop plant, including C4 grasses such as sorghum, maize, miscanthus, cane, and switchgrass. The level and specificity of transgene expression is assayed in hybrids.

In other embodiments, plants engineered according to the present invention to accumulate compounds useful for biofuels production or for forage or feed may be crossed to sorghum inbreds comprising the recessive mutant Inhibition of Alien Pollen (iap) allele that enables wide hybrid production. Progeny may be selected to contain constructs comprising the promoters of the present invention driving expression of transgenes allowing for the generation of wide hybrids with sugarcane and other C4 grasses to produce annuals or perennials with improved stem composition.

XI. Definitions

The definitions and methods provided define the present invention and guide those of ordinary skill in the art in the practice of the present invention. Unless otherwise noted, terms are to be understood according to conventional usage by those of ordinary skill in the relevant art. Examples of resources describing many of the terms related to molecular biology used herein can be found in in Alberts et al., Molecular Biology of The Cell, 5$^{th}$ Edition, Garland Science Publishing, Inc.: N.Y., 2007; Rieger et al., Glossary of Genetics: Classical and Molecular, 5th edition, Springer-Verlag: N.Y., 1991; King et al, A Dictionary of Genetics, 6th ed., Oxford University Press: N.Y., 2002; and Lewin, Genes Icorn, Oxford University Press: N.Y., 2007. The nomenclature for DNA bases as set forth at 37 CFR § 1.822 is used.

"Crossed" or "cross" means to produce progeny via fertilization (e.g. cells, seeds or plants) and includes crosses between plants (sexual) and self-fertilization (selfing).

"Elite line" means any line that has resulted from breeding and selection for superior agronomic performance. Numerous elite lines are available and known to those of skill in the art of plant breeding. An "elite population" is an assortment of elite individuals or lines that can be used to represent the state of the art in terms of agronomically superior genotypes of a given crop species. Similarly, an "elite germplasm" or elite strain of germplasm is an agronomically superior germplasm.

"Exogenous nucleic acid" is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells that can be cultured into a whole plant.

"Plant" refers to a whole plant any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant.

"Recombinant" in reference to a nucleic acid or polypeptide indicates that the material (e.g., a recombinant nucleic acid, gene, polynucleotide, polypeptide, etc.) has been altered by human intervention. The term recombinant can also refer to an organism that harbors recombinant material, e.g., a plant that comprises a recombinant nucleic acid is considered a recombinant plant.

"Transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Yield" is the culmination of all agronomic traits as determined by the productivity per unit area of a particular plant product of commercial value. "Agronomic traits," include the underlying genetic elements of a given plant variety that contribute to yield over the course of growing season.

Having described the present disclosure in detail, it will be apparent that modifications, variations, and equivalent embodiments are possible without departing from the scope of the present disclosure defined in the appended claims. Furthermore, it should be appreciated that all examples in the present disclosure are provided as non-limiting examples.

EXAMPLES

Example 1

Identification of Genes Activated in Association With Stem Starch Accumulation

Sorghum stem composition was analyzed using near infrared spectroscopy (NIR), a spectroscopic method for analysis of biomass composition (Wolfrum et al. (2013) Multivariate Calibration Models for Sorghum Composition using Near-Infrared Spectroscopy, Technical Report, NREL/TP-5100-56838), and gene expression in stems was analyzed using RNAseq, a method developed by Illumina for preparation and analysis of RNA expressed in cells based on sequencing DNA derived from RNA isolated from one or more tissues, from pre-flag leaf to post-grain maturity. This analysis revealed the onset of starch accumulation in stems just before grain maturity and extending several weeks post-grain maturity. Suites of genes that are activated post-anthesis, some prior to, and others in parallel with, starch accumulation in sorghum stems were identified, together with their promoter sequences.

Table 1 lists sorghum genes that encode or regulate enzymes involved in starch biosynthesis and degradation in stems. Other genes having expression patterns useful for the design of grasses that accumulate high levels of starch in stems are also identified in Table 1. Promoters and promoter regulatory elements associated with these genes are useful for stem-specific gene expression that provides low expression in stems pre-anthesis, followed by induction of expression after anthesis and a subset with peak expression approximately at grain maturity. Promoters and regulatory elements of these newly-identified genes can be used according to the present invention to regulate expression of genes that result in the accumulation of starch in stems of grasses to produce plants and plant lines useful for biofuel or biomolecule production and for forage.

The genes listed in Table 1 were identified by analyzing gene expression (of sorghum stem RNA isolated from plants at 8 stages of development: (1) Vegetative pre-flag leaf (pre-anthesis) stage; (2) when flag leaves are expanded (10-14 days before anthesis); (3) at peduncle booting (7 days before anthesis); (4) anthesis; (5) ~14 days post-anthesis; (6) at soft dough stage of seed development just prior to grain maturity; (7) 10 days after grain maturity (PGM1); and (8) 35 days post grain maturity (PGM2). Relative expression of the genes in stems in Table 1 varies >50 fold at the pre-flag leaf stage and >50-fold at maximum induction of mRNA levels post grain maturity demonstrating that the promoters associated with the identified genes can be used to drive transgene expression at an array of levels. For example, a promoter element having a particular temporal expression pattern can be chosen from the genes listed in Table 1 to drive expression of a transgene at a desired level. The group of genes in Table 1 show low levels of expression pre-anthesis and 10-fold to >100-fold increases in expression in stems post-anthesis. Therefore, proteins encoded by transgenes expressed using the promoters of genes listed in Table 1 will not accumulate to significant levels in stems pre-anthesis nor to high levels during early grain development, minimizing secondary affects on vegetative growth and grain set. However, the genes will be activated post-anthesis, driving the accumulation of useful compounds in stems.

TABLE 1

Genes induced in sorghum stems post-anthesis.

| Gene ID | Function | Anthesis | PGM1 | PGM2 | Increase |
|---|---|---|---|---|---|
| Sobic.002G322000 | Glucose-6-phosphate/Pi translocator | 63 | 1510 | 1392 | 24X |
| Sobic.002G075800 | Seed Imbibition 2 | 10 | 932 | 904 | 89X |
| Sobic.009G245000 | AGPase Large subunit | 10 | 545 | 217 | 54X |
| Sobic.006G066800 | Starch branching enzyme 2.2 | 17 | 513 | 323 | 30X |
| Sobic.001G044800 | Raffinose Synthase | 2 | 235 | 280 | 162X |
| Sobic.001G236400 | UDP-Glycosyltransferase superfamily | 4 | 190 | 324 | 88X |
| Sobic.001G396400 | bZIP Transcription Factor | 0 | 157 | 90 | 466X |
| Sobic.004G282900 | Major Facilitator Superfamily | 3 | 30 | 28 | 12X |
| Sobic.010G047700 | Starch synthase | 3 | 98 | 88 | 34X |
| Sobic.004G071200 | UDP-Glycosyltransferase superfamily | 3 | 17 | 73 | 27X |
| Sobic.001G290400 | NAC domain protein 71 NAM-2 | 3 | 77 | 32 | 22X |
| Sobic.001G083900 | Starch Phosphorylase | 2 | 48 | 13 | 22X |
| Sobic.004G120100 | Phosphoglucan, water dikinase | 5 | 19 | 13 | 3X |
| Sobic.002G202700 | WRKY76, expressed | 1 | 17 | 14 | 20X |

*Numbers in Table 1 represent relative transcript levels in stems pre-flag leaf formation, 10 days after grain maturity (PGM1), and 35 days post-grain maturity (PGM2). The genome sequences, and gene names listed in Table 1 are publically available at the Phytozome v9.1 website maintained by the Department of Energy (phytozome.jgi.doe.gov).
**The genes listed in Table 4 are induced in stems post anthesis and may also be used according to the methods herein for transgenic expression in plants.

Figure 2:
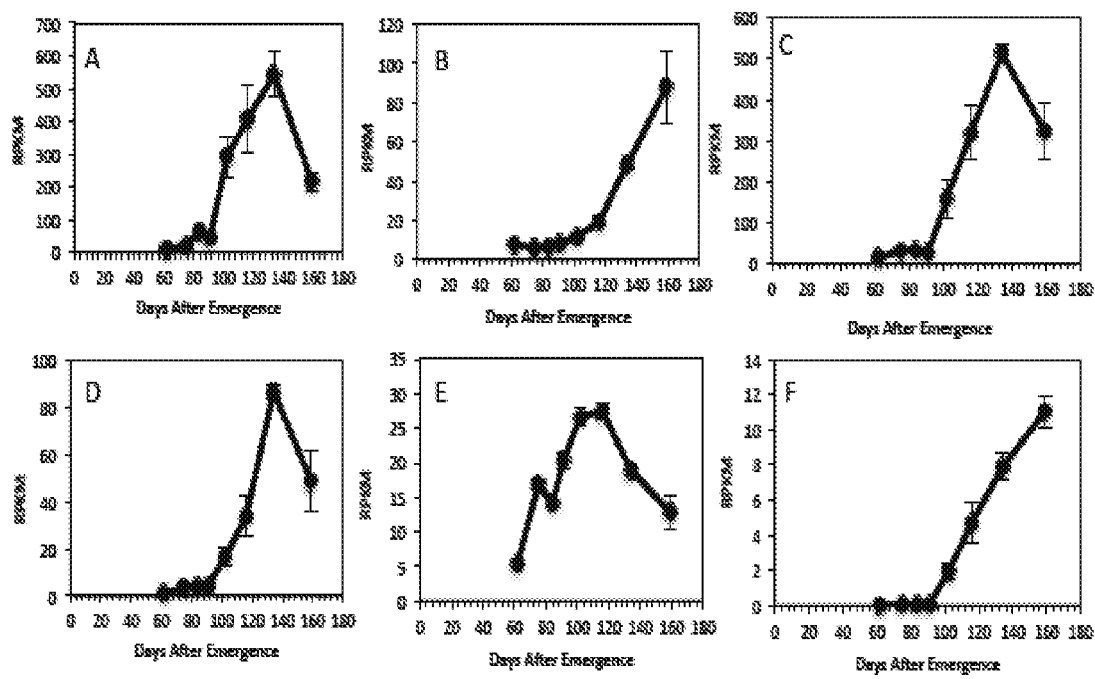
FIG. 2 shows expression of key genes post flowering in the sorghum internode, which are involved in starch biosynthesis and degradation. Expression is measured in Reads Per Kilobase of transcript per Million (RPKM) over 0 to 180 days to flowering. Genes induced: (A) AGPase Large Subunit Sobic.009g245000; (B) Starch Synthase 2, Sobic.01g093400; (C) 1,4-α-glucan-branching enzyme, Sobic.006G066800; (D) α-glucan water, dikinase Sobic.010G143500; (E) Phospho-glucan water, dikinase, Sobic.004G120100; and (F) β-amylase, Sobic.002G329400. Error bars represent SEM, n=3.

Expression profiles of promoters and genes involved in starch biosynthesis and degradation in sorghum stems was evaluated, and is shown in FIG. 1 and FIG. 2. Flowering occurred approximately 70 days after emergence and grain maturity at approximately 105-110 days. The list of genes in Table 1 and FIGS. 1 and 2 may be expanded according to the methods provided herein using additional RNAseq analysis and qRT-PCR analysis.

Example 2

Identification of Promoter Sequences Activated in Association With Starch Accumulation The genes listed in Table 1 are tested for specificity of stem expression by analyzing expression of the corresponding genes in different plant tissues and stages of development. Regulatory elements present in this suite of promoters are used to optimize expression levels, tissue specificity, and timing of induction of endogenous or heterologous coding sequences.

Example 3

Identification of Sorghum Promoter Sequences Having Useful Expression Patterns

Table 2 lists sorghum promoters identified by the present invention as having useful spatial and temporal expression patterns for modifying stem composition. For example, the promoter sequences identified in Table 2 may be preferentially expressed in sorghum stems, or may be useful in the design of grasses that accumulate high levels of starch in stems.

TABLE 2

Promoters with useful expression patterns in stems during sorghum development.

| Gene ID | Function of Regulated Gene | SEQ ID NO: |
|---|---|---|
| Sobic.001G044800 | Raffinose Synthase | 8 |
| Sobic.001G083900 | Starch Phosphorylase | 6 |
| Sobic.001G236400 | UDP-Glycosyltransferase superfamily protein | 10 |
| Sobic.001G290400 | NAC domain containing protein 71 NAM-2 | 9 |
| Sobic.001G396400 | bZIP Transcription Factor | 7 |
| Sobic.002G075800 | Seed Imbibition 2 | 12 |
| Sobic.002G202700 | WRKY76, expressed | 13 |
| Sobic.002G322000 | Glucose-6-phosphate/phosphate translocator | 14 |
| Sobic.004G071200 | UDP-Glycosyltransferase superfamily protein | 3 |
| Sobic.004G120100 | Phosphoglucan, water dikinase | 5 |
| Sobic.004G282900 | Major Facilitator Superfamily | 4 |
| Sobic.006G066800 | Starch branching enzyme 2.2 | 11 |
| Sobic.009G245000 | AGPase Large subunit | 2 |
| Sobic.010G047700 | Starch synthase | 1 |
| Sobic.001G174100 | GRAS family transcription factor | 17 |
| Sobic.001G396400 | Basic region/leucine zipper 53 TF | 18 |
| Sobic.003G396600 | ZOS5-12 - C2H2 zinc finger TF | 15 |
| Sobic.009G180500 | Myb-like HTH TF | 16 |
| Sobic.002G360100 | ZOS3-12 - C2H2 zinc finger TF | 19 |
| Sobic.002G368700 | OsMADS18 TF | 20 |

*The genome sequences, and gene names listed in Table 1 are publically available at the Phytozome v9.1 website maintained by the Department of Energy (phytozome.jgi.doe.gov).

Example 4

Expression Patterns of Novel Sorghum Promoters

Promoter sequences derived from the genes listed in Table 1 or the promoter sequences listed in Table 2 are fused to reporter genes (e.g. GUS, GFP) to form constructs used to transform plants. In some embodiments, the constructs comprise a fragment or variant of the sequences disclosed in Tables 1 and 2. The specificity and timing of gene transcription driving by the promoter sequence is determined from the transformed plants. In some examples, sorghum, maize, *Brachypodium*, rice, and other grasses are transformed using *Agrobacteria* or particle bombardment to determine the specificity and relative activity of various promoters for use in these and other target plants.

Example 5

Expression Constructs Comprising Novel Sorghum Promoters

Promoters of the genes listed in Table 1, promoters listed in Table 2, or fragments or variants thereof are fused to the coding regions of genes (or alternatively full-length genomic sequences) to increase the accumulation of compounds encoded by the coding sequences in stems. Transgenic plants (T0) are generated and analyzed to confirm stem specific expression of the transgene at the correct stage of development and target tissues. Plants are selfed to create homozygous T1 plants for further testing. If transgene expression occurs in stems, it is determined whether increased gene expression results in significant accumulation of end product. In certain cases, more than one coding sequence is expressed to induce high levels of end product accumulation. If this is the case, then two or more genes required will be expressed in stems using the suite of promoters derived from genes in Table 1 or the promoter sequences in Table 2. While starch accumulates in sorghum stems, it may be useful or necessary to express transcription factors (TFs) that activate the starch biosynthetic pathway in other plants that do not normally accumulate starch in stems or to further increase starch accumulation in sorghum. TFs useful for this purpose are included in Table 1 and Table 4 or in more extensive lists of genes induced in sorghum stems post-anthesis.

Example 6

Expression Constructs Comprising Novel Sorghum Promoters

In one embodiment, selected promoters of the genes listed in Table 1, promoters listed in Table 2, or fragments or variants thereof are used to express an RNAi construct targeting the mRNA of glucan, water dikinase (GWD) for degradation or translational inhibition. Methods of reducing RNA levels of GWD in leaves using RNAi have been described (Weise et al., 2012). The present invention therefore provides transgenic plants expressing RNAi sequences specific for sorghum GWD in stems (or the ortholog from maize or other grasses) to reduce GWD activity and the rate of starch degradation in stems post-anthesis. These transgenic plants accumulate significantly higher stem starch content without affecting growth. Up and down regulation of orthologs of SEX4, beta amylase, and other enzymes involved in starch degradation are also be targeted using RNAi expressed in stems using promoters associated with the genes listed in Table 1, the promoters listed in Table 2, or fragments or variants thereof.

Example 7

Modification of Promoters Driving Expression of Enzymes Involved in Starch Breakdown Grasses and other plants that accumulate high amounts of starch in stems post-anthesis are engineered by modifying elements in the promoters of GWD and other genes that encode enzymes involved in starch breakdown in stems post-anthesis, for example as shown in Table 3. In certain embodiments, promoter sequences are modified using non specific-mutagenesis (i.e., EMS, X-rays) or targeted mutagenesis (i.e., zinc finger nucleases, TALEN, or CRISPR technology).

TABLE 3

Relative expression of genes encoding enzymes involved in starch breakdown in sorghum stems during development.

| Gene ID | Function | PFL | FL | Boot | Anthesis | Post Anthesis | SD | PGM1 | PGM2 |
|---|---|---|---|---|---|---|---|---|---|
| Sobic.001G226600 | β-amylase 1 | 0 | 0 | 0 | 1 | 2 | 3 | 1 | 3 |
| Sobic.001G293800 | β-amylase | 126 | 13 | 7 | 6 | 3 | 3 | 5 | 6 |
| Sobic.001G372100 | β-amylase 3 | 56 | 3 | 2 | 2 | 1 | 2 | 1 | 2 |

TABLE 3-continued

Relative expression of genes encoding enzymes involved in starch breakdown in sorghum stems during development.

| Gene ID | Function | PFL | FL | Boot | Anthesis | Post Anthesis | SD | PGM1 | PGM2 |
|---|---|---|---|---|---|---|---|---|---|
| Sobic.001G508800 | β-amylase 1 | 1 | 1 | 1 | 1 | 2 | 3 | 6 | 10 |
| Sobic.002G136200 | β-amylase 7 | 13 | 17 | 23 | 20 | 14 | 11 | 14 | 11 |
| Sobic.002G329400 | β-amylase 5 | 0 | 0 | 0 | 0 | 2 | 5 | 8 | 11 |
| Sobic.002G329500 | β-amylase 5 | 1 | 1 | 1 | 2 | 1 | 2 | 3 | 2 |
| Sobic.003G003500 | β-amylase | 14 | 13 | 15 | 16 | 21 | 22 | 17 | 16 |
| Sobic.004G027800 | β-amylase 2 | 5 | 8 | 6 | 8 | 8 | 9 | 10 | 6 |
| Sobic.002G184500 | α-amylase precursor | 0 | 0 | 1 | 1 | 0 | 2 | 1 | 8 |
| Sobic.002G190500 | α-amylase precursor | 1 | 1 | 1 | 1 | 1 | 1 | 1 | 2 |
| Sobic.003G276400 | α-amylase precursor | 2 | 2 | 3 | 1 | 2 | 2 | 1 | 1 |
| Sobic.006G063600 | α-amylase precursor | 6 | 8 | 8 | 10 | 12 | 12 | 15 | 10 |
| Sobic.004G120100 | Phosphoglucan, water dikinase | 5 | 17 | 14 | 20 | 27 | 27 | 19 | 13 |
| Sobic.010G143500 | α-glucan water dikinase | 1 | 4 | 4 | 4 | 17 | 34 | 87 | 49 |
| Sobic.003G358600 | Starch Phosphorylase | 2 | 6 | 7 | 10 | 23 | 38 | 90 | 40 |
| Sobic.001G083900 | Starch Phosphorylase | 2 | 5 | 6 | 2 | 33 | 41 | 48 | 13 |

*Numbers in Table 3 represent relative transcript levels in stems at different stages of plant development.
The genome sequences, and gene names listed in Table 3 are publically available at the Phytozome v9.1 website maintained by the Department of Energy (phytozome.jgi.doe.gov).

In one embodiment, promoter elements in the GWD promoter that are required for induction of GWD expression in stems post-anthesis would be targeted for editing using TALEN or CRISPR/Cas9 technology to inactivate or reduce the activity of these elements, thereby reducing expression of GWD in stems, but not in other tissues.

Example 8

Upregulation of Genes Activating Starch Biosynthesis

Grasses and other plants that accumulate high amounts of starch in stems post-anthesis are designed by transforming plants with constructs comprising the promoters associated with the genes listed in Table 1, the promoters listed in Table 2, or fragments or variants thereof, operably linked to sequences encoding enzymes for starch biosynthesis, or transcription factors that upregulate suites of genes that activate starch biosynthesis. The transcription factors that regulate suites of genes involved in starch biosynthesis may include genes encoding transcription factors listed in the Table 1 (i.e., Sobic.001G396400 bZIP transcription factor) or Table 4.

TABLE 4

Transcription factors that up regulate genes in stems that activate starch biosynthesis/turnover.
Transcription factor (TF) regulators of stem starch biosynthesis/turnover (AGPase)

| Gene ID | TF Family | Function | with Query | PFL | FL | Boot | Anthesis | Post Anthesis | SD | PGM I | PGM II |
|---|---|---|---|---|---|---|---|---|---|---|---|
| Sobic.001G174100 | GRAS | GRAS family transcription factor | 0.96 | 0.07 | 0.16 | 0.14 | 0.07 | 0.92 | 1.39 | 1.24 | 0.75 |
| Sobic.001G396400 | bZIP | Basic region/leucine zipper 53 TF | 0.93 | 0 | 6 | 20 | 18 | 34 | 113 | 157 | 90 |
| Sobic.003G396600 | C2H2 | ZOS5-12-C2H2 zinc finger TF | 0.93 | 1 | 6 | 6 | 8 | 15 | 17 | 17 | 12 |
| Sobic.009G180500 | G2 | Myb-like HTH TF | 0.92 | 7 | 8 | 16 | 13 | 45 | 51 | 83 | 64 |
| Sobic.002G360100 | C2H2 | ZOS3-12-C2H2 zinc finger TF | 0.92 | 0.04 | 0.10 | 0.28 | 0.16 | 0.31 | 0.58 | 0.67 | 0.51 |
| Sobic.002G368700 | MIKC | OsMADS18 TF | 0.87 | 25 | 50 | 51 | 52 | 102 | 102 | 154 | 107 |

*Numbers in Table 4 represent relative transcript levels in stems at different levels of maturity.
The genome sequences, and gene names listed in Table 4 are publically available at the Phytozome v9.1 website maintained by the Department of Energy (phytozome.jgi.doe.gov).

Example 9

Production of Hybrid Sorghum Plants With Enhanced Biofuel or Forage Properties T1 plants engineered according to the present invention to accumulate compounds useful for biofuels production or for forage or feed are crossed to elite R-lines (pollenators) and/or A-lines (seed parents) for hybrid sorghum production, followed by introgression of the engineered element/gene/RNAi into elite backgrounds. Comparable inbreds are used to construct maize hybrids or other hybrid plants. The level and specificity of transgene expression is assayed in hybrids.

Example 10

Production of Wide Hybrids With Enhanced Biofuel or Forage Properties

Plants engineered according to the present invention to accumulate starch in stems post-anthesis are crossed to sorghum inbreds comprising the recessive mutant Inhibition of Alien Pollen (iap) allele that enables wide hybrid production. Selection for progeny that contain constructs comprising the promoters of the present invention driving expression of transgenes will be followed by generation of wide hybrids with sugarcane and other C4 grasses to produce annuals or perennials with improved stem composition.

Example 11

Production of Plants With Enhanced Levels of Mixed Linkage Glucans

Mixed Linkage Glucans (MLGs) accumulate in vegetative organs and in some plants, to high levels in seeds Like starch, MLG accumulation would improve the biomass composition of stems for use in bioenergy and forage applications. CSLF, which encodes an enzyme for MLG synthesis, has been identified and is expressed in sorghum stems. In addition, genes that degrade MLG have been identified and are expressed in sorghum stems, at increased levels post anthesis. The same regulatory elements/promoters, transcription factors and methods described above for engineering starch, could be used to engineer increased accumulation of MLG in stems. Promoters that enhance gene expression in stems post anthesis could be used to drive increased expression of CSLF in stems post anthesis. In addition, RNAi constructs expressed using promoters that are activated post anthesis could be used to decreased the expression of genes encoding enzymes that degrade MLG in stems, leading to high levels of accumulation.

TABLE 5

Relative expression of genes encoding enzymes involved in MLG synthesis and MLG degradation.

| Family/Feature ID | Functional Annotation | PFL | FL | Boot | Anthesis | A + 11 d | SD | PGM1 | PGM2 |
|---|---|---|---|---|---|---|---|---|---|
| MLG Biosynthesis | | | | | | | | | |
| Sobic.007G050600 | CSLF6 - beta1,3;1,4 glucan synthase | 215 | 188 | 318 | 241 | 164 | 146 | 121 | 62 |
| MLG Degradation | | | | | | | | | |
| Sobic.006G070400 | endo-1,3;1,4-beta-D-glucanase | 17 | 23 | 20 | 12 | 13 | 8 | 7 | 4 |
| Sobic.009G129800 | endo-1,3;1,4-beta-D-glucanase | 59 | 52 | 37 | 61 | 76 | 106 | 125 | 132 |
| Sobic.009G129900 | endo-1,3;1,4-beta-D-glucanase | 29 | 20 | 26 | 27 | 23 | 34 | 41 | 30 |
| Sobic.009G130000 | endo-1,3;1,4-beta-D-glucanase | 2 | 2 | 5 | 8 | 5 | 22 | 5 | 15 |

*The genome sequences, and gene names listed in Table 5 are publically available at the Phytozome v9.1 website maintained by the Department of Energy (phytozome.jgi.doe.gov).

Example 12

Production of Hybrid Sorghum Plants With Enhanced Biofuel or Forage Properties Sorghum lines comprising constructs comprising the promoters associated with the genes listed in Table 1, the promoters listed in Table 2, or fragments or variants thereof, driving expression of transgenes for production of starch in stems are crossed to elite sorghum inbreds optimized for production (i.e., high yielding, optimal flowering time, large stems, capable of high stem sucrose accumulation). The elite sorghum lines are further enhanced through marker assisted breeding for quantitative trait loci (QTL) that increase biomass yield and have optimal stem traits (large volume, non-lodging) and sucrose and starch accumulation in stems. Sorghum lines engineered as described above to accumulate starch are crossed to lines with enhanced potential for starch accumulation, and progeny with enhanced production capacity are selected to create improved inbreds or hybrids.

What is claimed is:

1. A DNA molecule comprising a DNA sequence operably linked to a heterologous transcribable polynucleotide molecule, wherein the DNA sequence is:
   a) a sequence selected from the group consisting of SEQ ID NOs:1-20;
   b) a sequence having at least 95 percent sequence identity to a sequence selected from the group consisting of SEQ ID NOs:1-20, and having gene-regulatory activity; or
   c) a fragment comprising at least 500 contiguous nucleotides of any of SEQ ID NOs: 1-20, and having the activity of any of SEQ ID NOs:1-20.

2. The DNA molecule of claim 1, wherein said DNA sequence has at least 97 percent sequence identity to a sequence selected from the group consisting of SEQ ID NOs:1-20.

3. The DNA molecule of claim 1, wherein said DNA sequence has at least 99 percent sequence identity to a sequence selected from the group consisting of SEQ ID NOs:1-20.

4. The DNA molecule of claim 1, wherein the DNA sequence comprises a sequence selected from the group consisting of SEQ ID NOs:1-20.

5. The DNA molecule of claim 1, wherein the heterologous transcribable polynucleotide molecule comprises a sequence encoding a protein involved in starch biosynthesis.

6. The DNA molecule of claim 5, wherein the protein involved in starch biosynthesis is an enzyme or a transcription factor.

7. The DNA molecule of claim 1, wherein transcription of the heterologous transcribable polynucleotide molecule in a plant suppresses expression of a target coding sequence.

8. The DNA molecule of claim 7, wherein the target coding sequence encodes a protein involved in starch breakdown.

9. The DNA molecule of claim 8, wherein the protein involved in starch breakdown is selected from the group consisting of: glucan, water dikinase (GWD), β-amylase, and starch phosphorylase.

10. A transgenic plant, plant part, cell, or seed comprising the DNA molecule of claim 1.

11. The transgenic plant, plant part, cell, or seed of claim 10, wherein the plant is a monocot.

12. The transgenic plant, plant part, cell, or seed of claim 11, wherein the plant is a C4 grass.

13. The transgenic plant, plant part, cell, or seed of claim 12, wherein the plant is a sorghum plant.

14. A method of expressing a transcribable polynucleotide molecule comprising obtaining a transgenic plant according to claim 10 and cultivating plant, wherein the transcribable polynucleotide is expressed.

15. A method of producing a transgenic plant with increased starch content in stems post-anthesis, comprising the steps of:
   a) transforming a plant cell with the DNA molecule of claim 1, wherein the heterologous transcribable polynucleotide molecule confers increased starch content when expressed in stems;

b) regenerating a plant from the plant cell; and c) cultivating the regenerated plant.

16. The method of claim 15, wherein the plant is a monocot.

17. The method of claim 16, wherein the plant is a C4 grass.

18. The method of claim 17, wherein the plant is a sorghum plant.

* * * * *

SEQUENCE LISTING

```
<160> NUMBER OF SEQ ID NOS: 20

<210> SEQ ID NO 1
<211> LENGTH: 3000
<212> TYPE: DNA
<213> ORGANISM: Sorghum bicolor

<400> SEQUENCE: 1
attcatattt tttttgaagt caacaccgag atcctcacct gagttcattt caattcatat      60
tgtaaaggta gattttgaaa ggcagtgaca atatccaata cagagttaca gacacaagag     120
tacatatgat gcctctattc tttgacata ttttaattta aactcaatcc tactgataat     180
ttaaatatat atcaaatcct cttaaggcac ctaaatgact acttaggcct tgtttagttc     240
gcgaagggaa aaatttcgcg acactgtagc actttcgttt gtttgtggta attattgtcc     300
aaccatggat taactaggct caaaagattc gtctcgtcaa tttcgaccaa actgtgcaat     360
tagtttttat tttcatctac atctaatact tcatgcatgt gtctaaagat tcgatgtgac     420
ggagaatttt gaaaaatttt aggtttttag gtagaagtaa acaaggcctt agataattgt     480
tctaactata aaagttcata tgtacccatt tacactaaca tactcccttt tagaagacag     540
gagcattact atattttgt aatgctcgtg tccctagaa aggagtaaag ctcatgctca      600
tggagagttc atatgtattt aattaagtat ttaaaaatat ttgaatacta catgctacat     660
gcattgcgcg ttggatggag gttgaagaag aagctaacat gtgagcccca cacgtcagtg     720
agaggaggaa gggagacaca acaggggtat tttaggacat acaggaatac cgtaggctga     780
gtccaacgtc gttgaatatg tagaaaatgg cacgattcaa gctgaagaag aattataatg     840
acatgtttca aaatagacga atagtaatgg tattttttcca aacttgcaaa attgtaatgg     900
tctcagtcaa aaaaaaactt taattaacat gtgctctctt tcagtagaca tgagcattaa     960
aaaaatattt atattaattt acactcattt tctcgatgca catttcctaa caaaataggc    1020
acatacagac attcaaaaat aaataaataa ataaagacat tcaaatatag gcacatatgt    1080
actctgtaat cggtatccaa tcatgaagat ttaccaattg ctgtctatat gcttttttcat   1140 ccatatccat atattagcca tatttttttt cttttgtatg acacattatt gtatcttcaa    1200
tatgcattat ttcaaacttt agcttaaatc atgggtgact gttgtagcat cccatgtacc    1260
atgaagttat gaatctagct tttgttttta aaattttaat cttcttactt gctacagatg    1320
ttttgttctc atgttaagtt gaattttttt atctaattct gaatctagct tttgatttcc    1380
aagtttcaat tttataatga tctagttgcc acacctcaat ttctagacac aacaacctca    1440
atgttgtagg gcgacgagct tgcttagtcg cttccatata ctcactatgt tccaaaataa    1500
ctatcattct cgcttttcga gaatcaactt tgattaatat atattaaaaa aatattaata    1560
cttatgttat ataatttgta ttatcggaaa gatctttgaa tctagtttttt ttaataaaat    1620 ttatttggag atgtaaatgt tacacatatt tttctataaa tctagtcaaa ctcgcgacac    1680
```

| | |
|---|---|
| gcaaacctaa aacgacgatt attttgggac agagaaagta tatgactttg catttcctct | 1740 |
| ccgttgaaat gttgtcaacc tcaccgtttt ctgatgacat gttgaagtgt acggtcacga | 1800 |
| cagaaagagc aagcgccatt gcacggcgac cacacaatta aagaccggga accagtaaa | 1860 |
| caaatgcacg tcataaaaaa tcgagtttta ttcatgcaca atgctgcctg atattgctgg | 1920 |
| gaactgagaa gcatatgttt tagagcattt tcaaaagtct cttttaaact catcttttat | 1980 |
| attattattt gaagaaacat ttgaataaga gtcattcact atatatttcc atcttccaac | 2040 |
| attttttata tcttgtgtca cttttgaagag tcatttctgc actccatctg ccgttagcga | 2100 |
| gaaaccaaag aaatagagag tgataatatc tagtctagat acctaattgc accaaaaaat | 2160 |
| agatgttctc attaatacgt gagaatataa cgtctttgct ggtctaagaa atcatgacta | 2220 |
| aaaataatat tcgctaattt attataaaaa aatactatta gctgctagaa taagtacgtc | 2280 |
| ttataagaca aacgaactga gctgtaccaa cgtgaaattg tgctcgctgt aattctgttg | 2340 |
| ttaaatgaat taaggccgat gctccctcta ttctaatatt ttttattttt tagatatatt | 2400 |
| ttttattaca catttaacat ataaacatct tagatatttt tttacaaata aacatttttag | 2460 |
| aatttagaat agagagagca cctatcggcg aaatggcttc cagcaaattg caagtcacgc | 2520 |
| tacacaaagc tgtggtgccg agggagcaat gcagagctac tggcacccag cttgatttgt | 2580 |
| gaacatgcac aagaaacagg cgaaaacacc cagatttcat ttcacgctcc tcctgccacg | 2640 |
| taggcccaaa acgagggaca gaggaagcac atgcagcgtt tccccgaaag acacgtaaag | 2700 |
| cagagcgtct cgtctccgag gacgacaccc cgttcacgag ccaccggtga atcaggcaga | 2760 |
| gccaatcttc cccacgccaa cgctgccact gaaagcgctt cgacctcgtc cgtccgtccg | 2820 |
| tccgccgcga ccccgctcag cttcccgtgc cgttttttgt ggctggcagc ctggcgccac | 2880 |
| cccacctgtc cacttcctcc tcgactcggc gaggagtccc cggatccgtt tttgctgtgg | 2940 |
| gtgcttctcg aatcaaacaa accaaaaacc cctcctcgcc tcccatcact tgctacgcca | 3000 |

<210> SEQ ID NO 2
<211> LENGTH: 3000
<212> TYPE: DNA
<213> ORGANISM: Sorghum bicolor

<400> SEQUENCE: 2

| | |
|---|---|
| gcctgtgggg acggcccgat catgggacgg gagtacgggg caccgcgacg agccgacgac | 60 |
| agcgatggat gctcgctggt tgctgcacgc ccgccttctc ggctacggct agtatatagg | 120 |
| agcatgcgca tcatgtacgc ccgctgtacg ctcggcggtc cgctccattg gcgcttttt | 180 |
| cataggagta cagagtactg ctctctctc tctcctctcc ctttcgatca gcggagcggc | 240 |
| ggtccgcagg ccatgtgtat ggcacgacag gtttgcatgg ctgcgttgcg gaggtccgga | 300 |
| tccaccaggc cgacgacacg tacgacgtgc cgccgtgcgt agccaagcga tcgaggccag | 360 |
| ctagccgtcg tcgcgccatc gccttcgccg gatcggacgc caacaactct cgctgtcacg | 420 |
| acgctgtgcg tgcggtgcgg tgccaacttt ttttgacgtt agcgtacgcc caaaataact | 480 |
| gcgtatttcg ttttctttt ttttagtaa tcaaactttt tagacaaagg ccctattcga | 540 |
| ttgtgtttat tttgcagcgc tgagcgacaa ccagtagtag ttgcaaatga gtgcagctga | 600 |
| acaagcttaa taattaatac tttataaatc tcgtaatata tatattatga aaatatattt | 660 |
| tcttacaatc taataatatt ttttatttat atttagtcaa acctaaaaaa aaattaagcc | 720 |
| agatataaat tctgacgtac gtatgcgagg cgaagtgagg cgatgagtcg acctcccaac | 780 |
| tgattggttt gcaacttcgc atgattggtg tccaaccact gagctactca cctggcagtg | 840 |

```
ccatatactc cctccgataa aaaaaaaata taaatctcac attttgaaaa gccaaatagt      900
ttatacttaa gtattttttt tatgaaaaag tactaacact tttgagctaa tttgggtacg      960
gatcttatag ttatatgttc ttccgtggac agaaggatta ttatgtagta tgagcaagat     1020
atgtgtgttt aatgacgcaa gtgaataaat taagggtgtg ccaaacccca tcgacgattc     1080
ttaaaatctg ttgatccaga gccatccatg acccgtgctc tgtaaagctc agcttcaatt     1140
cggccctcgc catcattaac taaaagaac gagtggcaca gtggctattg gttaccaatg     1200
atccaagggc caaagcccaa acgccagtgg taccagtact aagattagca cgtgcaaact     1260
cactccatcg tccatcccct ggaccatcgg ggcaaaacca aaacgttcag ccggacagca     1320
cacctatgcg agaggccctc tgcgtcacct ttatttgcct cggccagatt ccctttcccg     1380
agacatccaa ggagcacggg ctctgagtcc gagtgacggg gacgggccgg ggaggtccat     1440
gggcccacac acacacacac acaccacgcg ggacgcccgg acaagcggtt cgatcgcccg     1500
cgacgcgact cgcacaggcc cggccgccac ggggtcggg ggcccggacg accaaaagat      1560
cctcggcgcg cggcgggcag cggcagggcc cacggcggcg ggcggggcag gtccggtacg     1620
ccgtggcgcg cgattccaac cgtcaatttc cccggcgatg tgtcccaccc acccacccgt     1680
cctgtactgt gatcgcccat cgctctggac ctctgtggtt tactgccaca agacgggaga     1740
aatggacacg ggccacttgc tcttgctctg tgccgtcggc cagtgaggaa acagtgcacg     1800
gctttgttct ccaccgtgct actgaatagc gatgattgag cctttgtagt atagtaaagc     1860
ttgacattgg ccgcatggta agaccggagt tggcgccgaa gcaattgtaa gtcaattaac     1920
aggctactca tcttgggatg acacacatta ttctataaat ggatgcctcg gttctagaga     1980
tggatgtcta ggtacttgct tcaactctta cctcaacatt atttgacata agccttgagg     2040
ggtgtttagt acgtaagatt taagatctca tacaaattta gttcttgtct tgtaatattg     2100
taaaatgcaa tagactttgt aataaggttg ctgattgttt agcaacctat ggagcatgtt     2160
tgttggcttc tggctcttat tcaagccata gagtttgtaa catcactcgt taatggcgat     2220
ttgcctagat atcatgccct aatgcagttg tgtttcaaaa aaacaaagac cggagttggt     2280
gggcactagg caagtttcga tcggtcactc ttctaatttc acggcgaact aaacaagacg     2340
tatttgagtt tttattttg ttttttcctt aggtataagt tgcatctagt aggttcagct     2400
ctgttcgttt gaatttattt tgtaataaat cagtgaacaa tatttttag tctggctttt      2460 cagttaagtg tatgtttgct ttctacttgc acatgagtga agagtgatc ccccggctaa      2520 ctcaagtacg aattctattc tgggccgaaa atttcggata tggccatatg ggaagaagag     2580
attttcacct ttgtaaacaa acctttcatg tgaatggaca cgcatctaga aaagccgatt     2640
agagcatctc caagagacta gccaaatcat tttctaaagg tatatttggc tattgttgaa     2700
ggaaaaacgt ctctaacaga ctctgtaaat gactcttcaa atttagtagc tcttcatcct     2760
accatatttg ctctctactt ttggatagcc tacctcatta gccatccttt tgcagagtct     2820
gttggagtaa tctaatattt ttttatcaaa actattttag agagtagcta aatcagtaaa     2880
tttgggctaa tattttttggc taatctctct tacagtctac tacgtactct agctcctaaa    2940
aagtaggtga cactgcattc caaggacaag gaacggccaa aaatcttcat ctcacgtcag     3000
```

<210> SEQ ID NO 3
<211> LENGTH: 3000
<212> TYPE: DNA
<213> ORGANISM: Sorghum bicolor

```
<400> SEQUENCE: 3
tgattcttcc ttgaaccaaa cacacttata aattatccgt ctcctccaca gcgccggcgt      60
cctcggcagt gaccattaat ttgcttcgtt gatgtggatt actggattct ctttgttgca     120
tttgcctcgt tgtatggttt gctggctctt tttttttttt catcctcagc cattcaccgt     180
tggctaccta ctagtggtac ggtcctagtt cctctccggc cgattcagca atcaacacca     240
tactttcgtg atttccttaa tgtcaacatc attctagcca atatcataca cacatcccca     300
aagtgcacaa atggcattgg ccaaccgaat catatgcaca tcatcatcta aagggtgtt     360 catattttag ccacggctat tgtgtttgtc catcatcaaa atggacaaat catcgtactg     420
tatatggtct tgtatcattt tatttacttt tcaggtatcc atgctcgttt ttattatatt     480
tacaccaaat tatcatgcga attcaaaggt gctcatagct agggataaag tgcatgcgca     540
tatattcata gtaggtaagt gtacatacat atatgagtgt acaacacagt ggtgtacata     600
catgtatgat ttttcaagga aaatatgaa ttacaactat ttattgttga tgtttaatta     660
gcccatcacc gacaatgagc tagatcactt gatgtaggat ctaaccgact ttgaggtcag     720
ctggtgccta gagaatgtat gcactcagac cttatgactc tagcgatgag cacgatacgc     780
aagacacgtc accgaaggag cgctaggagc gcgatatgcg agagatccta acgaggtctc     840
ttgagaccca aaaccccaca tacctaggaa ggaacccgcg gggtgtgcag cggctatggt     900
ttgccctagc tagcttggcc gatctagagc ttcgtcatcg ttgatccacc gtccatgcag     960
caccgttgaa gaacaaagga gaagtagagg aaagagagt aaaagagagc ttgtagatta    1020 attttgtga tgattgtgtg tgttggacac ctaaatcggt cgtggacttt atatttataa     1080
ggtggaggtg gccttatccc tctaggagtc gaaacccatt ccaaatttca tcaaaacacg    1140
gtttgatctg ttctatctga caaagtcggc aaagctgatt tgggaatcgg ctagccagtt    1200
tctatgggca cggagtgttg tttctaggct gaaaacaggg ggctgacttg ccactaggaa    1260
ttctcggtaa aaaaacttcc aaaattcata actaactcat gacaattatg tgttttgggc    1320
acctcaatcg atcgtgaacc ttatatttat aaggtggagg tggccttatc cctcaaggat    1380
tcgaaacccc ttccgaatct cgttaaaaat gtgtttagat ccattttgaa cttgacaaag    1440
tcggcaaaac cgacttggga gtcagctagg ccggtttcta caggcccgga gtgatgcttc    1500
tacgctaaaa ataggggaag tcgtcggtag ctgacttggc actaggaatt ccatgcaaaa    1560
agtttcacaa attcataatt aattcattca gactccaaat gagatgatct atgtatgttt    1620
tttcgatcag ctcgacgata agaacacaat gatgaaagtc taattttgta ttcaagaaag    1680
ttaggaattc agcttagctg acttggggag tcggctaaac cgactctagt tgagttagtc    1740
ctcgaaaagg tcgtttcctt cagtcgggct tcaaatgcaa tgttccaagt atgctttctt    1800
gtcgtcttga tgatagaaac atgatggaga gtccattatg cactttgaac acttttgagt    1860
gtcaacattt atcttagtgg atgcttgttt cctacacaac tagaatggat caaccattct    1920
tattttgagt ggatggttgg ttttacatga ttattggaac atattagtat gtagtcatca    1980
tgtattaggt tttttagttt tgcatttgac catgttttac tactctattt caatttataa    2040
gtcgttagcc aattctctac ttttggacaa atttataaaa aaaagtatat taacaaccac    2100
tatatcaaat aaattaaact atatttcatg gtgtattaat agaccttatc taatgtcata    2160
gatgtttatt tatttatcta taaacttaat taaaacttga taaaatttag cttaggtcac    2220
aaccaactac tcccaccatt ctcttttata aggcttgact tgatatcaca cggtcttcct    2280
aattaaactt tgaccatcta tttattttat tttatctatt atttataggc acaaacttat    2340
```

| | |
|---|---|
| gataattgga caatagattt aattacaaat gtaatcatca tatcaagttt gtgttataat | 2400 |
| aattaaatat cattagttaa attattagtc aataattttg aagtttgaat cttcatttgt | 2460 |
| gtgtgtccta taaaagataa tggatgtagt aaaacaactt ctacaatatg gcgagtgtct | 2520 |
| ttggccttgt ttagttagag aatgaaaatt ttttggatgt tacatcaaat gtttcgtagg | 2580 |
| atatcggaag ggatgtttat atactaataa aaatctaatt acataactcc agaaacggag | 2640 |
| agacgaattt attaagccta attaatctat cattagtaca tgtaggttag tgtatcattt | 2700 |
| aaggctgatc atagactaac taggcttaaa agatttgtct cgtgattttc aactaaactg | 2760 |
| tatagttagt ttattttta tttatattta atactctatg tatgcctcca aacatttgat | 2820 |
| ctaatgggtg aaaaatttt agattaggaa ctaaacaagg cctttgtact caacttaaat | 2880 |
| tggtagtacg agtagatctt aactgcacaa caatcatacg cgccaaccta aattaaattg | 2940 |
| tgctgtcgga tgattcgtgt tgtgtgtga caaatccgag ctgagcctga gagaagtacg | 3000 |

<210> SEQ ID NO 4
<211> LENGTH: 3000
<212> TYPE: DNA
<213> ORGANISM: Sorghum bicolor

<400> SEQUENCE: 4

| | |
|---|---|
| gaaaatatta tctttgttta tgtatgattg ttatcattag atgaatcata gaatgtattg | 60 |
| gatcgataca aatgttgcta ataaaagaaa tttatccgac aatgacattt ttctttaggg | 120 |
| cgatggaggg agtacttacg aaagttgcac ttttttttct tagtgtgcta gacacactgt | 180 |
| acctaactaa catcgtgtct gctaccgtat tagtttatct cctcatgacc ttgatcttca | 240 |
| cgtggaaatt tcaagatctc accggaatgc tgtcattgta ttaaagcaac actacttggt | 300 |
| cccgaacaat ttcaactaac atgtgaacga aagaatgttc gttgttctga aacttcacat | 360 |
| taatacaaag tggactgcga agcttatgat ttacaggtaa atggccgatc gagatcatac | 420 |
| aaagggatta cacgtggcgc ttgcgatccc tagcaggtac cgatttcaca tgccggtatc | 480 |
| gtaagcaggt acgtactgta catagcatgt acagtaagca tgttcgccgc atctttggag | 540 |
| attctgtatc aaaaatcgtc cccagctttt tgctaggagc tacagtactg atcgggactg | 600 |
| aaaaaaatga ggcggttggc ctctctagcc tccgcggaaa gacgacgagg ctttggcctt | 660 |
| ttggatattc tcgggtttat tccctgattg actgacagag tgacagtctg catccaagca | 720 |
| tttttttttc catccaaact ttacatcagt gttccatcgc aaagtactac atggcacaga | 780 |
| aattttgcgg atactggatg ttggattctg gatgttaacg acgaaagtga tgggaaacaa | 840 |
| gcgttgtcac gcgattggtg gagtagaagc cttgtttagg ccttgtttag ttcagaaaaa | 900 |
| ttttcaagat ttcccgtcac atcaaatatt tagtcgcata catggagcat taaatataga | 960 |
| caaaaataaa aactaattac acagtttatc tgtaatttgt gagataaatc ttttgagcct | 1020 |
| aattactctg tgattggaca atgtttgtca aataaaaacg aaagtgctac agtagctaaa | 1080 |
| aaccaaaaac tttttcaagat tccccgtcac attgaatctt acgacatatg catggaccat | 1140 |
| taaatataga taaaaacaaa aactaatttc acagtttgcc tgtaaatcgc gagacaaatc | 1200 |
| ttttaagcct agttactcca tgattagata atgtttgtca aataaaaacg aaagtgctac | 1260 |
| agtagcaaaa tctaaaaaaa ttcgcaacta acaaggcct tacactgtct acgtcgagga | 1320 |
| aaaaaaatgt aattctcatt tttgagcaat tggccaaaac tatattaaaa agtacttaca | 1380 |
| ttcataccgc aaaaataaat atcattaaac taatttttaaa aatatttttca taatatattt | 1440 |

```
atttagatac ataaatacta aaattattta ctataaactt ggtcgaacta gtttgacatc    1500
tcataattat attcttttgt gtatggaggg agtacttcct ccattcacaa aatatgcaat    1560 tctactttt  ttggttagat aatttaaaat ttaactataa ttatataaag tactaatatt    1620
tatgatataa aataataagt attaaatcaa ttatgaaata tgttcttata gtaagcctat    1680
ttagactttg aatattaaaa ccatttttat aaacttgatc acagttaaat tagtttgact    1740
atgtaaataa atatcataat tatattttg  gatggattag atagaaaata aaatatcaat    1800
actccatgtt tgttaagaaa aatagtggca gttcgcaatt tgttatagtc taaagacaaa    1860
gagagattct ggtgtttaga agcttacaac tacatcaaat aaaaaaaaat aagaagtctc    1920
aaccctcaaa cttaagtcta gcccacaaca tgttttcaag gcatgttttc cttttgacct    1980
ttaggacaag tttgcaaaac atacattagt tttgaagttt taatatatt  caggtcgaaa    2040 cgccacctat ttaggaagac aaataacagt ctttagcaac tttcctcatt gttgttgata    2100
gagttgtgct aactattttt aatcgttgag gttggaaatg gttgtttatc tagtctaggt    2160
cttctttttc tttatcttta ttattaagta atcagtaatt tttcttgcct aatttgtttt    2220
aaaaaggaac tgtaatgatt catattacag ggcatgacat taagagaaat ggtgatttac    2280
tttttatcga ctactcaata aagcacaaaa gatttattct tccactctga ttctctgata    2340
tctgaatcac caagaagcta gtatgcttat taagaccttg acagtgacta cctttgtata    2400
aatgttgatg aattgtatcc ttatgaatcc atatacctag ctattttatg atgttatatt    2460
atatcattag taaattacat cccttaggtc cgtactctaa tgtttaaaat catgatccg     2520 ccactgctac gaagcaatat attacattga agtgatcctt ttttttaag  aaaaagaaag    2580 taattctatg ctaaaagtca tttctcgcaa ataaactaga ggccaggagc tgaaagccat    2640
agagaatcac ttctcctgat tcatttctcg cacaaaacca cttcttatat cgagttcatt    2700
gattctagaa aaatcataga gaatcgcttc tcacttgatt atgaccaaga ggagacctac    2760
gaaatacgct tggagctcga tcacgtgata cgcggtatca taaaacattt tgcggttgat    2820 ttttttttt  aaaaaaaga  acatcttgcg gtgcagtctc attgaacagt ccgcgcgccg    2880
tgtgtgcgcc gaaacgaaac ccaaccatct gggccgatga atcggggaaa gaaacaggag    2940
cgaggaggag cagaggtcag gggtggcgag gcattttttgg ccacagggcc gctgccaaaa   3000
```

<210> SEQ ID NO 5
<211> LENGTH: 3000
<212> TYPE: DNA
<213> ORGANISM: Sorghum bicolor

<400> SEQUENCE: 5

```
cccgacaacc acgcgtgcgc cgactccacc accatcggcg tcacagtgca ctcgcgcctg      60
agcccctcga cgagcgcaaa cgctcgcacg tgcaccgcga catgcgggta ccaccttttg     120
cctttccctc gctcctcttt tgccgtaaaa aaagatagca agtcgcaacg cacaactggg     180
cagaatttat atttttttct ggcacaaata acagcaagta cctacagcgc gtacgctcat     240
caacagcaag ttaggcaccg tctatttgca tggcgaatat ctacactatg agccaccgtc     300
catgtatgct gccgcaccgt caatctgctg cttgtactat cattcttgtg catcagtcat     360
ctcaggcacc cagcacgaga accgccattg atggcgaagc aaccaagatc accggacagt     420
gccctcctct ggcctataaa agccaatgcc gagcagcact actccaccat gccaaccacg     480
ctaaccacac taagccgttt gctctgcgtc cactcactcg cttatctcct tgctcagaga     540
gagctgcacc ctgtggatct cttttctctgg gctacagtca gcaaggtagc tagcctccat     600
```

```
caatttccta cctctcctat ctctcttcat gttcttgtat tcgagaacgg tggtctaaac    660
cgtcagctag cccaagcttt cacggccagc aatggcggac gagcacgaac gattaacgtg    720
gtcactcctc tgcctctctg tcctgtccac tacctcctct cctttcgttg tctcct tata   780 gtcttaaata ccaaatcaga atgctgacca aagtacacca cgctcacaca gctcacgtca    840
acgccctcct ccgaaaagtc ttgtttattt tagtagacaa cgatcttgta aatttaatgt    900
cttcttcatc tgaactctgg tttcaacgat tctttgttct aaattcatct aaaatcacga    960
tctaccaccc attttaattt cattatttt agggcttatt tgaatttatg tgatttatt     1020 atctgtgctt attgtctgtg tcgatcgtca catattttag ctgatggagt gaacgagccg   1080
gagaacgagg acgttggaga cgagtaccgc gagttcgaca ccgaggatcc gaactgtcag   1140
ccaggagttt gccgcggacg ccgacggagg caagtccaac caattccctt tgatgcatag   1200
atcttatttt taaacacaac ccgtaaaagc cgatttaaat attgcatgta ccatatatgt   1260
acgagatatt ttcgctagtt agttaaaacc tgttgaatag tcatccttga attgatatta   1320
cccgataatt gtcttattca aacctagaaa aaaaatatta tgctaacaga aatatcatta   1380
tttaatatgc ttaggacttg ttactaatcc tggatactca tcgctatatt ttctcaaata   1440
taatgatttt aaaagaaaaa ctgtatgagt aggtgaaaat gaattatggg tattgtgaaa   1500
gggttagtga acaagttata gatgtgatta ctatagagat ggggccgatg ggatcccttc   1560
tgggatgccc tggtgttatg gcttatacct tgcggggtta attgggaaga tatccgcctt   1620
gtctcgatta aggactgagt tgattattca tcttgtctaa ctcatttatc gtacgactac   1680
tcgccttgta tgggaaaggc ttagtctcaa tccctctagt tagtatggca atcacctaga   1740
ggcaggtgtg caatgggaca ctaagagagg tatgtgaaat ggttgaaata tatgaaatat   1800
aaagagctct gtgaattatt gtggtatcat aagatgtggc cttagtgttc ccgtggtgag   1860
cgtcattact tagctatgga gggtaatgac tttgatagat ctgtgcttgc acaacggtgt   1920
aagttatggt atcctactta tggtgaaagt gtacaacctc tacagagtgt aaatctatct   1980
ggatagctgt gtccgcggtc tcggacgggt tatggtttgg tttcaacaat tagatgggtt   2040
gggatgagta aaaacatgag agtgagtgtg attttgaaaa taaatggttg actgccattg   2100
tgttgtgaga acaagggttc aacaacactt aaaattatga tcaaacctcc attttagaa   2160 atactatcat atatgaaaa agaggtcttt tacaaaaata tttgtgaaac aaaaccttgc   2220
gtgtgtaaaa agatagcttt atgcatataa aactaagcct catccttgat ttatgcatat   2280
gcatatatat tgttatcatc ttccacagga taaggttgaa tttgctgagt acgttgtact   2340
catccatgct ttgacccgga cttcgattcc gaagtggtgt tcgagtaagg tcgtgtctgc   2400
acccaacaaa gcctgtggca atgggactcg tcagatgttc ggttatgata tcgtttgttt   2460
ctgggtcctt tggacatatg ttgtattttg gtgtcttatt attatagcgt gccttcattg   2520
tctacgctta tcgagactac aacgtagaaa cttatctaat gttactagcc tcctagaact   2580
agtattgtat cacatttgag ttcctagttt accaggggcg cttcaggact caacatacac   2640
caaataacat gaataatatt tttcaaaaca ctacattgca ttattccata taagtgcagt   2700
tcaaatttga aatattcaaa aaaatcaac caaacaaaat aaattaagaa aatattaaa    2760 aaaggtcaaa atttgcctaa atttaaaat tgagtttcca ataatatatt ttaccaccac   2820
aaaaactagg cttaaaaaat ctaaaaaata atttgccgag gtctaccct cggcaaagaa    2880 tcttttttta aaaataaaa aaatttaccg agggccttat atatgggtct cggtaaagtt    2940
```
ttcaacccta gatcccaatc gagccggcaa aaaaaagcta cgcgcagcct attccttctc  3000

<210> SEQ ID NO 6
<211> LENGTH: 3000
<212> TYPE: DNA
<213> ORGANISM: Sorghum bicolor

<400> SEQUENCE: 6
agctcgggag cttgcctggg cctgaaatgg ttgtcgtcta tgaagctgct attatctttt  60
tttaatactc catccattca aaaaaaaata caattccagt acagaaatct taaggttgac  120
cagcttcag cttaaaaatt ataatattta tgatatcaaa taaatgctat tatattaatt  180
acaaaatgta ttctcataat aaactgatgg agccactgat gtaaatatta tttactagaa  240
acttagttaa atgtgaacca ctttaactat cacgcgactt ataattgcat tcttttgaga  300
cggagagagt atagtccttc tatttatgtt tgctcgggag cagtgcactg cagctttaca  360
ttttactct tgccctgccg cctgcctttt taaacacaga atacaaaagg ttgctaagtt  420
gctaacagtc accatagaaa ggccatagtc actgtaatga ttgttatgat tgtcttagag  480
caactctaat aataaccctc aagacaaacc cttacatttc gtttgagggt tccccacttt  540
gaggccctgt tttctaggct acacttcagt agtgaccctc aaataagtgg accgagggaa  600
aagaccactg gtcgctaaag gagttgagat cacgagtgtc atggtgggga gtctcgatcg  660
cttcccttt acctccctat gccaaacaca ctcaactgca agaaaccaa acaacagaat  720
catgctagac atagacaata gatcgggtgt ccgtgcacta ggaaacattg tcttatagg  780
atggaggacg acgtgacttc cgacaatgaa gactcgggtg gctagtttga gttccctttc  840
ctgagccggg aggtggcggg gggaggggcg ctgacatcgt cattgtggtg gccgacaagc  900
tctttgcgag cggccgcatc tgagtgttct actcggtgtt tggttgagtg atggacgggg  960
tgtgtgggat ataactcggg atacctcaag gtgagacatg ggtcgcacca tcggaggtgg  1020
tctagcccac aagatcaaga tgtatgatgc atgacaccga tcggtgtgca ccgtaacgct  1080
tctagaagat atgatttact tggactctta tagatattgt aatccaaata ggatacctac  1140
catataacta actagaatat ttttcttgta actcaatccc tccaaagtat ataagaagag  1200
gtacgggtcc tctagtcggc atccatccat agatcttgat accttaatac atccatcgac  1260
acataggaca taggatttta cgttacattg atggcctgaa accgtctaaa tattgtgtct  1320
cagtgcttgt attgccatct gattcctgat cacgcgcacc tctgccaaac aatctaccat  1380
cgtgggcata cccctcggtg gactgctgac gagatattgt cgacgcgagg cctagcgtca  1440
atgctaaggg cagttatagg gcagttatgt gggcctgaac gacatgtccc tggatagcta  1500
atgcctcaga acgctcgggt catcgcctgc atcctcgccc tcgaggccat tgcagaggag  1560
aggatttgca tgtggagtgg tcggtgaata ggagctatga ctcaaacatg tcagcagaga  1620
agccacacca tgcatgccat atccctactt gagcctccat aactggatgt gggtatctag  1680
aaacatgtgc cctgccgaag aagatgagat acaccttcac agaaggtctc tatctctagc  1740
taccacaaat ctatttata tatgtgcatc aaccttcctt attgcttca tctttatgac  1800
ttacctccct tgccatgag gacatcacta atctcagcac atgcccccgg ctccattgag  1860
agcttatggc ctaatttgga accaaagaga ggtcaaacca tggatgaaaa gttgctttag  1920
agaactaaat ggcttattca ataacgttc tcacgagtta tcatgcaac aaaaaatatg  1980
agatactaac aggatttgac tttccaaact agcctttga gtcgatcacc acccaccatc  2040
cctctctaat ttgcttccac caccatgccc aatataattt gcttcgtttc tcactcattg  2100

-continued

```
gccacttata tctcccttct caactccaat gacgcaacta ttatcggttc atcggttgtc    2160
agttgtcaca ctcaacttcc ataactatta acttgtccat agtaattcta tcaccgtatt    2220
taggttacat aattggggat cactctccaa acaccctctc cttccaacaa tatcgctatt    2280
tgccattctt gccaccctag tgttaaagtt gttccaaggc cgaagggtct acaaagaccc    2340
ttgtgacatc gaccccacaa ctcaagtttc atcagagaag aacatgatgc atatagatat    2400
agatgaacat cgatttagtg ggtggagaat gtgtacaatc caatgtacaa aattcaactg    2460
atagtggcca aaaaatccaa catcaccatg aactgaatcg tgcgacgagg tggtcctact    2520
actaagtgtg cagtgtccgt cactcaaatc gtttcaccgt agtctcaagg aatcgctaga    2580
gaacaggcaa attgcaacaa actcaacaat gtttgtcttt tcatttggtc cgcagtccgc    2640
gttaccatac agcatgaagt tcagaaaaca gaatgactac aaaaaggcca aaatactctc    2700
gaaaaaggac ttcgaagacg aaaacaacaa aagcatatac aaacaaaatg atcttggaaa    2760
cgcgggaaat gagctttatt aggtgaagaa gctttcacaa aagacggtga gtcatttacg    2820
gccgtcgaaa aatgtgacaa gtagcttcag aaaaggagga cgattctcag ccgttgaaat    2880 gcggagaag gatacaaact gacctgaacc acgcggccca tcgggcgctg acgtgggccc    2940
accgaccagt gccacagcac gtgccctggc caccgtcgca cggagccacg gacacttcag    3000
```

<210> SEQ ID NO 7
<211> LENGTH: 3000
<212> TYPE: DNA
<213> ORGANISM: Sorghum bicolor

<400> SEQUENCE: 7

```
ctcattccca tctccagatt cacctaaaat gattctactc ctatccggga gagaataacc      60
aaaacattat cctatccctg ttattccccg tgaaataaat gctcgagata ttttggttac     120
taccacttgc tacattattc taggagggtg agtgctctga aaaaaatacg aggaaataaa     180
aaggggcaag tgcccggaac ctcgaagaaa agaaaaagtg agacgagagg taaaaatgga     240
caagtgtccg acagtagaat taggggtaca agatacccac ctgagagaaa agaaaaagaa     300
aatatagagc atctcattcc cctcgaaaag cttcaagtgc aagaaggta tgtatctcct     360 taaaagaaca aaagtagaat tagacttttca ccattgtcat caccctacac cattcattcg     420
ccacacatgc acatcttgat attgacttat tgacttattt ctctagatcc atggtttaac     480
tatgcaataa atgtcttcta agtatgtata ttttatctcc cacctatgag ctccagatat     540
caagccttat tagaataggg tgagagagaa ggcaatgtca ctatgcctca taccacaaat     600
accacatact ttgagagaag gcatatacca tcacagcctt ggtaaggatc cagaaatacc     660
acaaaagaga gactagagag agtcatacaa ggattctctg agttttattt tgaaaatcta     720
caaaaactcc agagctatag ctaattaaga ataagagaca tggcgcttga ctagactgtt     780
ctatctttta actgctcaag acacaagtga cggttgcaat ccccatggtg aaaggtaaaa     840
tgagtaagtt ttaagtctta acagtttacc ctaacccaga gatgagatct tgcttgaacg     900
catgtgtact tttaaggcat gaaaccactg cagaaactct tgagtccatc cttgctcagg     960
gacgagcaaa aggtaagctt ggagtagttg ttgacggtcc ttaagtatca tatttaatca    1020
tcaaataaat aaagaaaagg atccaaatgc aaccaacacc tagacttagg gttttatcta    1080
atagaattcc acgagttttg gtgtttgtct atttctacag ggggtatca ggaaatacgg    1140 aggaaaggcc catatgtcgg gtttacatag agatattagc gtgccgcgta attttctctc    1200
```

```
atctagaaga ctccagaagc cacgggaacg aacgtgtagg cgatcgggcc cgagggcagg    1260
gcgcccgccc tccccctagg gcgcccgccc tgagttagag tccaatcagg accggtctcg    1320
cggattacgc tccaccgacc taaaggatca aggataaccg ttcaatcaat gtcggtttga    1380
tccgacaacc cagattcact tgaggggact atataagtag accccctggc ccctggagga    1440
gaacaagttc attgtagagt tgagaggtgc cctcgaagga taacctttcc tctacataga    1500
cagagcaaaa gctagggttt ggagatgaga gctctcctct cttctctaaa ctagagtaga    1560
tctagatagt agcgacatgg agagcgaggg aggattggag gagaggccgg cctgtcggtt    1620
cttcctccgg ttgtacttcg ccatgatcaa gctctaatca agcttgctca tgggatgact    1680
ctggtaatct acttctatatt cattatgcaa ttactattca tgtatgttct ggttcacaac    1740
tcttttgagt acttttaatc tataggaccc tataggttag agttgtagta taggtgtaag    1800
cgtggtgctt agatctagat tacttgtgga tatcccctgt ctaactggat cgtgtggtag    1860
gccgcgtagg tgacagttac gttggtcccc tgtagtccac ctcctgttag caggacgggt    1920
agggtttatc agcctatgga taagcatcct ttgtgatgta ttcttatcac gtggttcgtc    1980
ctagacatag acatacccct ctaaagtaga gaaacgatag ttatcctctc tattctccta    2040
ccatcgccca tatattagat tgctctactc tctattccca tattatcacc cattgttatc    2100
ttacctttaa tattgttctt attcaattct accatctttc ctatttacac ctacctatct    2160
atctaggtta agttagagca tagatcagtt ctcccgtttt cctgtggata caataaaatc    2220
tttaaccggg taaaagctac aacggtatcc gtgcgcttgc ggatttatct gtgtgcgtat    2280
aaataccata gtacactcta gtgccatgct ggggatgaca acctagtatt caagtggtgt    2340
tagcaagtgt caacaatggg cggcgggtgt gggtgaggat gggccgcagc tgaagattgt    2400 ttaggggtttg gctgacactg actagtgggt cctctaaatt ttagtgtgcg ggagtgggct    2460
gggccaagcg cgccaaagtg aaaatgggct ataccgaccg atggttggtc tctaagatat    2520
atctttagcg tccgatgttc tgacgcggat tcgtagcgac cgatgttctg ccctataaat    2580
aattatagcg accaatgatc agttacaaat ttatagcgat cgagggttca acgctaataa    2640
taagttttag cgtccattgt ctgacggtat agattggcta cgttgcggta aatatgcatt    2700
aaccgctgcg ggcgtgttat gttgacagct acggttaata gattaactgc agcggacacg    2760
ggcgtccgcg acgcgtttgc ccgctgcgga aaagggaaaa cgcccgccac ggttattttt    2820
tctggagtag tgttcgtctc gcaaattaca ggtaaactgt gtaattagtt tttactttta    2880
tttatattta atgttctatg catatgtcta aagattcgat gtcactgtga aaaatttgc    2940 aaaaattttt aaagtaaacc aaggccctga ttctcaccgg cctggagaga cacgctcaca    3000
```

<210> SEQ ID NO 8
<211> LENGTH: 3000
<212> TYPE: DNA
<213> ORGANISM: Sorghum bicolor

<400> SEQUENCE: 8

```
atttcgttca agaattttat tttattgcga ttctagatac aagtcaaatt tcggtgaatt      60
tagtgaggcc ttagtttgca aaatttttag ttttttttgg ctattgtagc attttcgttt     120
ttatttgaca acattgtcc aattacagag taactagatt taaagattc atcacacaaa     180 ttacaggtaa actgtgtaat tagttttat tttcgtctat atttagtgct ccatgtatgc     240
gaccaaagat tcgatgtgac gaaaaatctt aaaatttttt gcgaactaaa caaggcctgt     300
gttaatttat agaaaataat atcaatattt atgcctctaa atacaactat atgtttatga     360
```

```
taacgatact tattcagtat tattatagac gtcattaatt tttttaccaa tttagttaaa    420
ttgaaaatta tttgattcct caaaaataag aattattaca tgtctgaaat acaaaacatg    480
cctcgcattt atccatccaa gattttgaac caagtgtcca tttgaggaag gttgagttga    540
actaagacat tattctgtca caaatcaaac aggataaggg taagcacgca tgggatgtga    600
ttcgttccca acagcaacgg gcctgaaagc cgattaaaaa ggattggttt gcgtttaaag    660
ttggctgaga aactggaatt aacaaccagc gaaacctcct tgtcaaaaaa aaaaaaaaaa    720
aaacagcgaa acctctcatc gtgtgtgtca gacagacaca tgctcaaaca atcacaagaa    780
ctaaggccat gtttacttcc actcaaaaac ccaaaatttt tcaagttttt ccgtcacatt    840
gaatctttag acgcatgcat gaagtattaa atatagacga aaataaaaac taattgcaca    900
gtttggtcga aatgtacgag acaaatcttt tgagcttagt tagtccatgg tggacaataa    960
ttaccacaaa taaatgaaag tgttacagtg tcgcgaaatt tttctcctca ccaactaaac   1020
acggtctaag gcgttattta gttccgaaaa ttttttgagaa attgacactg tagcgctttt   1080
gtttgtattt gattaatatt gtacaattat aaactaacta gcctcaaaag attcgtctcg   1140
tcaattccga ctaaattgtg caattagttg ttattttcgt ctatatttaa tactctatac   1200
gtacgtctaa aaattcgatg tgatgtgaaa tgtgaaaaaa tttgcaaaat tttctgaaaa   1260
ctaaacaagg cctaaagatt ccaatcaatc atggccgaga ccggtgtttg cttagacgac   1320
gccgcttggc gtctgctcga ccgttgtttc ctgagaatgg ggtagaaaca tttgactagt   1380
tgcataatga ttgattgagt gctgattggt ttctggaaaa tggtttgccc cagaaaataa   1440
tgttattccc tccttctact ttactctgtc cgtccgtaat gttttgatca caaaaaaagg   1500
gaattttgat caacaaccgt tcaaattaca aagcatcatc agtacaattg tatttggaat   1560
atctctgaga tgagatatta tagtactgga tttttttttat caatcgacaa cacattataa   1620
gagaagtcaa aggtaaattt taaactatcc agatgctgga tagtttaaaa ttgaagtagc   1680
caacattaat tgtaaagcaa acttgtataa ctttgcccca agacaatcta accttgtgtg   1740
gccgcagata aacagtttct tagctgcttc taagaaaacg taccaagccg tggttagttt   1800
ggcaatctgt gtcttttcac tatcaaacag tgcagtggtg ttctttctta ttcaaatgtt   1860
cttcagacaa tgcgacagaa gagagtaaac agtactccaa gtctccaaat cttagcaaaa   1920
ttgtttggtc tctctggtgg ccagtgcgat atgcaaagtt tccaaggttg gtcacttgaa   1980
cttctctcgt accatcagtt ttcgctacta gattgtactg aaattcttca gaaaaccaat   2040
tttcgttttg cagatattcc gaaaaaaaaa ggaattcctc aaatcaaaag tatagagacc   2100
ttaatttgag gattactgtt tggacaagcc cttatctgct ttagcatgtc aaagaaacgt   2160
agcaaagctg tggatagttt gacaatctct tgtcttctcg ctatcaaaca gtggtgttct   2220
tgttgacagg ttctgcagac aaggctttcc agacaatgca acatcagaga gcaaaataac   2280
actccaaatc ttagcaaact gatttggtct ctctggtgtg ctgtgcgata tgcaaagttt   2340
ccacggttag tcacttaaat ttctctcgca ccatcagttt ttgccaccag tacgtgttgt   2400
tcttgttcag aaattcttgg tgtatcttgt tttgcttgca gataatctgc caaaaagaa   2460 gtagtgcctc aaaaatacag caaagcaccc tccaaaacct tcagcaaaac gattccaaca   2520
gcgagctgac aagacaacca agatacacca aaatcaggca caaatcatca ccgattcatc   2580
atagctggcc tcgaaggctg gaacattcag gccttgttta gttcgcaaaa ttttttgttt   2640
ttgggtactg tagtatttcg tttttatttg acaaacattg ttcaatcacg gagtaaatag   2700
```

```
gttcaaaaga ttcatatcac aaattacagg taaactgtgc agttagtttt tattttcttc    2760
tatatttaat gctccatgca tatgaccaaa gattcgatgt gacgagaaat cttgaaaatt    2820
tttgcgacct aaacaaggcc tcattcactc tggatgcttc acgagggaca cccaaaaagc    2880
agcaccaaaa ataacatctc tcctccgggg cccacatgcc agttagactg agagagtaca    2940
caactactag agctgagtta gcctgtatat tctgcaacca tctcccaaga tccccatcct    3000
```

<210> SEQ ID NO 9
<211> LENGTH: 3000
<212> TYPE: DNA
<213> ORGANISM: Sorghum bicolor

<400> SEQUENCE: 9

```
tgaaattgat caattttata gaaaagaaca aaaatactta caaaattaaa ttagcattat      60
tagatacatt ataaaatata gtttcctaat tcgctctttg atgtggtagg tattaatacc     120
cctatctatg aaactctcca taaactttga caaatttaga atattaagac aactcaaata     180
aacggaattc ataaaatggt gccatggatg tgttttacct acgaataaac aaaatttgta     240
aaaacggtgt catgtgcctc tcttttcttt cttcctttg ttttctttt tgcatctagt       300 atcccatatt tccccgtct cttccttctt gctgaatact atcatccatt gcaggaaaaa       360
aacaaaattg gagtgtcttt aacatgtcta gctccatatt attttgttc ataattatat      420 ttactgagtt atagtaaagt tgagtgagac tttatttag tggagtcaag ttaattaaat       480
tataagttaa agtgtgtttt tttgtaattt taagcagaga tggcgtagct aaaacttata     540
ggtgttcaat tcctcaaacg tactagaatt gcacaacacc ttaatctaaa tactaaatac     600
ttatagaacc caagatcttt tattacaccc tccattccaa attgtaaaat gttttttgtct    660 tctcaaaata ctatctataa aatgccttat aatttaaaac agtgagaggc tcgagctgga    720
agaagaaaga tccccccccc aatgtcaaaa tacaaaaata aaaatcaaca atgcatcaaa    780
ctctaacaat tattgacaat catcctcctc tgtatcaaga gaaaccgtat taagtaaatc    840
tctaaatcta tgtataagtt ttgaagccct tgcattttga aaagaactta aggttgtatg    900
catcttcaaa aagttcggcg ccagagacac ataaaaaaat ccaggtgctt gatagaaacc    960
tcccctcccc gtcccccaaa atactttgtt ctcctgtata ttttttcccc ctgcgagcaa   1020
agacagtatt tcatttctag cataaattgg gatcacgatc atttttgaaag agttgcaagt   1080 ttgcagctag gcaattgaat gaacaataat tctcgaatac acaaaaaaat tgtatatcat   1140
tgtagtagaa gagtttaaac aaacatacat acaatacgtt tctatcgagc gctgaaagag   1200
gtcaacctaa cacagctata gctgaaccat cctaacaaca gacctcttgt ttcaaccgaa   1260
agaataatgg aagcacatac atacttaaga tgcatgatat gctctattta gtggctcctc   1320
catgcacaga gaggtggtgt ggagtggagt caatatgaaa tgatcgaaga ggttgctgcg   1380
gcctctggtt taatggaaac ggaaagtgaa aagaaccgaa ccgagttcct gatgattagt   1440
ggtcggtcga cgcgatgcga tctgcacccc acaacttgct ctgcttctcc ttctccatct   1500
ccacgaccag cgactgctgc tccaaattat tgcgtcagca ttcacgctac gccgcacgtt   1560
tgcagtcagt tccggccata atgccacacg tgcgtgcgtg cgtgtatcat gcagtggcac   1620
gtggcagaga gagagaggtc aatttcagtt cagaacgaaa ctaaggtctt gtttagttca   1680
ccccgaaatt caaaaagttt tcaagatttc ctaccacatc gaatcttgcg gcacatgcat   1740
gaagcattaa atatagacaa aaataaaaac taatcataca gtttgactgt aaatcgtgag   1800
atgaatcttt tgaccttagt tagtctatga ttggacaata tttaccacaa acaaacgaaa   1860
```

```
ttgctacagt aacgaaatcc aaaaatttt cacatctaaa caaggcctaa agaagcatgc    1920
gaggtcaggc aaagcaaagc aagcaagcag agtagccatt tagccaagta caagatgggg    1980
gccagtgagg aggccaccgt gaaatgtaaa cggaatggac tagctaaggt ttccttattc    2040
agaaaaggaa atgtatactc aagaacctgg agacccaagt aggagtacat atcttattat    2100
gcatgtaata aaagtattaa aacaaaacaa agtggcgtaa tccggctgga agctgctaat    2160
ttaatcagtc gcgagtgtga acttaagctg taaaaaccaa gacaaaaggc aagtaagaat    2220
aaaactgggc ggtcacgaat cccatccagg acgtgtagtg tgtctggtgc tctaccgacc    2280
tcgctcatcc ccaaaaccag cgacggcgga ttaagctaag ctaagctaag ctaagcacgg    2340
atccaccaca atgacaaatt aaccaaaagt ttactcctat cctatatgaa ctgacaaatt    2400
tgcgcttttg agcgaggcgg cggcagcagc agccggctgc agttggccaa cagaacaggc    2460
aaaggactca gaaagcatgc ttgtgctatg gaaaatcgac taggaggagg actcagaaag    2520
catgcgtgtg ctatggtgtg tcccctttct agtttctagt atatacgtac tgtgtctgtg    2580
tgtcaatgaa ttggatgaaa cacgaggcaa tacgcatctg ctgccgcgtg tgtagtcact    2640
cactgatgaa ctcacctgga atgcacgtac gacacgaggg cttgacacgt tgggtgcgtt    2700
ggttattatt agttaactga atccagagca ttccagccag cggttttggc gagcttagct    2760
cctagctagt tgtgctctgc tgccgccata accatgacca tataaacgtg tgaaagtgaa    2820
acagttacgc ggctgcttga gaggagagga ggacgtttgg aattgcttgg ctcggacgac    2880
cgccgacctt gccctccctc gctttcccctt tccattccag cctcctccct gtccgtgtcg    2940
tctctgtcta tataaacgcc atcgccccgc ggcttctcac accctctcct cctcctcctc    3000
```

<210> SEQ ID NO 10
<211> LENGTH: 3000
<212> TYPE: DNA
<213> ORGANISM: Sorghum bicolor

<400> SEQUENCE: 10

```
ggcacagcga ccagagagtt cggtgggatc atagtaaaca ttagggcact cacaatgcaa      60
gactctatca cagagtccaa gacacttaat tacatattat ttatggtatt ttgctgatgt     120
ggcagcatat ttattgaaga aagaggtaga aaaataaga ctccaagtct tatttagact     180
ccaagtccac attgttcgag gtaataaata gatttagact ctatgataga gtctcacaat     240
acagactcta tcatagagtc taaagttatt tattacctcg aacaatgtgg atttggagtc     300
ttattttttc tacctcttca ttcaataaat atgctgccac atcagcaaaa taccataaat     360
aatatgtaat taattgtatt ggactctgtg atagagtctt gcattgtgag tgcccttaca     420
gattaattat tttgctccag cattgatcct ttgcatgcat gtattgaact ttggaaaggt     480
ttgcgtagct catctttttt aaccccgccg ttatgcgta gctcatacga gtattttgat     540
agccagcact agcatcagca aaagctata cgattagatg caaacacact gtgccacaat     600
atgattgaat aacaaagcac tttgcgcgct cacgcacgaa agtaatacca ggtaccgcat     660
gcgtgttcta atactagcgg gcacactatc actgatgctc cttattaccc tgaaaaattt     720
tcaccgatgc tctttaatat tccttaacac ataagcaatg caacttacag ccctgccagc     780
tgccacggta caatacgcac atagtactaa ggctctgttt agatgccaat ttttttttatt     840
ttgctactgt agcactttcg tttgtttgt acaaatattg tccaatcata gactaattag     900
gatcaaaaga ttcatcttgt gatttacagg aaaactgtgt aattagtttt tgttttcgtc     960
```

```
tatatttaat acttcatgca tgtgccacaa gattcgatgt gacggggaat cttgaaaact    1020
ttttggtttt caggtgaact aaacaagacc taattgaaaa tgacacatac tgtttctagc    1080
atttccctgc aggtaaggcc ttgtttagtt caccccaaaa agcaaaaagt tttcaagatt    1140
ctccgtcaca tcgaatcttg cggcacatgc atgaaccatt aaatatagac gaaagcaaaa    1200
actaattaca cagtttagct agaaatcgcg agacgaatct tttgatctta gttagtccat    1260
aattgaataa tattaaagtg ctacagtacc gaaatccgaa atcttttcgg aactaaacga    1320
ggcctaaaat tattggctat acgcgtcgtg gtcagttttt aatgttatct catcagacgt    1380
gacgccatgc tccaagagaa gcaaccaggg catctgaatc taatcacagt agaatatttg    1440
tactgtgggt tgggtagatc attaatttgc cgagaaaaat gcagtggcca cttgtccccg    1500
atccccgggc atgtacgtcg acctgaaact tagtcaaaat ttcacaattc atggttcagg    1560
taccacagta tcagccgctt gttaattagt gtaatttgtt cttgtttgtc tgatgtttgc    1620
tctatgctgc ttcgcagaag ccagaaggta aagcggccaa tctgtgcttc tggtcggcgg    1680
actaggcgcc aagtcatcat cgatggaagc ctcgtgtgtt tccttgttct tcattcaatt    1740
accgttggcc actcgggcgc tttgaaggac tgcaacgtgc atttgttgtg acgcagcaag    1800
ccgtctacaa gtcaagacaa aaggagcaaa attaaagaac acctcagcaa ctgtaaagaa    1860
tcaatgtccc ccgtgatgct tgcattgatg cttctatctg ctgccattgc atggagttgt    1920
ttaatttccc tccgatggtt aagttgtgta tagtattacc tagggttgga aaacttcatc    1980
agatcttttg atcccaagtt aaatatctca aatatgcttg cgtcatgagt gacaatattg    2040
atagaataga aacccgccag ttttttgtatt ggtgtgcttg ggaagtttca ggcatagttc    2100
tttggcatct ttggaaattt cacttccccc gtagcagacc agctgtccag ctgtacggtt    2160
aaaacaatat acaaacctaa aacatttcac ctgaccccaa tggagatgct tacgatcgtt    2220
ggcaatacgc aatacgaaca aaagatcagg tcccttgttt aatcaggcta gttggtgcac    2280
acgcaattgc acgagctgac taatattact gtattagtta gtgcatataa tacgtcgtca    2340
gttccctccc tccggtcctt aaatcttcgc cctccgccac cctcaggcca ccccttctgc    2400
cttcacaaat cttcttcctc tcgtcccctag ttgagtagag gcactgcaga gcacacagct    2460 cttttggttgt ttgggaagtg cagccccatg cctcctcctc ctcctcctcc tcctctcctc    2520
cggatgcctc acttcagcta gctagctagc taagttcctt cctgcttgtt tcgtgttcat    2580
ccgccaatct ccgtgccatg tcgctcacgg aggtcagcct ccacttctgc tacctccact    2640
ccctctccat cgtgcttctc tacttcttct acgtcatctc ctgaatcggc cgcctctcgc    2700
caagttccga tcgaacaaag ctaagctttg gtttgattca gagccgaagc tttgttcgtt    2760
ccaaacaaaa aattactact attgattact cctccatgct tgttcctctt cgttcttcca    2820
tgatgacccg ttcacgttca tctcccgggc ctctcttgct ttgctgctaa gttccgtgcc    2880
tctcctagcg cgcgcgtact cctacactca gatcgatcat tcgactagga gcagtgcgcg    2940 cttttttggca gtgtttgaag cagttaagta cgtgcttccc ttctgaaagt agtagctagg    3000

<210> SEQ ID NO 11
<211> LENGTH: 3000
<212> TYPE: DNA
<213> ORGANISM: Sorghum bicolor

<400> SEQUENCE: 11
tattactaag tcgctagtgt gaagtgtaac tatgtcggtt gtgtgagctt gtgacatggc      60
tgcctgtttg cattctagat tctcactagg ccttgtttag ttccaaaata ttttgggaaa     120
```

```
taggcactgt agcactttcg tttgtatata acaaatattg tccaatcata gaatatgctt      180
aaaagattcg tcttgcaaat tatagacaaa ctgtgtaatt agttatttt ttatctatat      240 ttaatgttta atgcatgtgt gttaagattt gatatatgag ggggaatatg aaaagttttg      300 caaattttt tgaactaaac aaggccctag atctcaaggc aaaggcttc cttttacacg       360 tcagcacatg atttcctatt gtaacatgat gtgctgtccc tctcttgatg ctatttgaca     420
gatttgggag ggacgggcat gtgcacggtg caggctcgct tgccattttg cgccgtgaaa     480
atttctggcg gcagagcaaa gagcagcgaa atatcagctc ggccgaattg acggtcaggg     540
aggagagcgc ggctggtcct aggcccatcg taccccggcc gggcctttc gtccgtttgt      600 ttctggtact gtgcggcgat ctggccgtgc tacgaaagca atcgccgata gggactgaaa     660
aaagtataag acggttgcca tcatccccta ctagtcaaca ccagtcgaca agctatagaa     720
aaatctccct cgtatctagg atcaacgagt gattaaacta ggcatgggtt gcacggctgc     780
acgctttctg gtgttggatg ataactaagg gtgtgtttag ttcaaaaaaa atacaaaatg     840
caaaatgaca actattttgg aatggtggaa tgcaaaatac caaaattttc acggtcatgt     900
ttagttccat ccaaaatgca gaatttattg ctcttatgaa agcctcttga gactcttttt     960
ggtttttttt ttttgtctct tgagggcaaa atccaaaatg gagaataaac acctttttac    1020
caaaagtttg acatggtatt tagtttcatt ttgcaaaatg attgaccaaa acctaaaaat    1080
ttttgagaaa aaagggagaa ctaaacaccc cctaattaaa atttgtgcat tattaggcaa    1140
gatgactcca agatgacagt agtggtgagt gagatactga gatctcgttg ctatagaagt    1200
gtcttgttta aaggatacat cataaggttt ggataatgtt tttcgtagct aatttggacg    1260
cgtggggaat ggaaacggac ggacatgtgc gtgaccagcg acagtggtag gtttttttt     1320 ttcattttgg tgaatcaccc ttgaagagct ccactaaaat gatgaatttg gcaccgctaa    1380
atctaccatt ccggagaatc cagatgtaga gtagaccgtt tgagtaacct ttagagcaag    1440
tattatagta agctgtaagc cgactaaata ttgaggtgga ggagagaaga aatgatagag    1500
aggagaagca gattgtaagc ttacatccag cttaggcaca ggaactaaga aactttatga    1560
gagagataag tggaccatgt attaatagtg aatagctaac tattgtatga tgagtgggct    1620
gagagaaggc tgaaaggaac cttacagcca acaaataggt tgtattatta acttgttctt    1680
agtagagtga aaactgtctt tggtgaatct aaagctcgtg gagttgtccc aaacgtattt    1740
ttaaaggtca tagcatgagg tttgaatgat gtttttatga aatcaaatgt aaaatatcga    1800
agggtacact cttcaggacc tctgtttaaa tgttacagca tgaggtttgg ataatatatt    1860
ttcatgaaat cgaatgtaaa atatacgcca ggtttgaatg atttgcttat gacaaggcaa    1920
ggattctcat ccgttagatt tgatggcct gcggcctaga tatcatctcc cccgggctgc     1980
gaacctacct ggcacgcagc aagcaaacaa atcctcagat atgctccttc gctcgccctc    2040
tagtccagtc taagatgttg tcactcgcgg acgagaacac tcgagcattc atctggaaac    2100
cctaatagac aggcacatga cagcgaacgc cagtacatga cgcacggtcc acgggcacg     2160 agcaagggcc gtccgtcgtc accaggcaca agaagacaca tgaacccat tgatggaaac     2220 acggcgcgag cgaatagccg tgactcttgt gaacggagga gctaaagcac gtcacctttt    2280
tttattattt attacgagcg agactccttt tgttcttctt aagactttt tgtttaacat     2340 atgtatagat tttataagat gaatctttta aatctaatta attttttaatt attataattg    2400 taaatatgct gcaatattta caaagttttt ttttcataaa ctaagatttt tcttttcact    2460
```

| | |
|---|---|
| ttttttttca taaactaaga cttttctttt cgtaaaaaac ggagagccag tagcttacgg | 2520 |
| gacttgtact ggtactgcac taccggcagc cggtagcggc agggctactc tagcgcaacg | 2580 |
| gatggccggg aacgcgctcc cagccgttgg ttcgcgatct gctgctctgc tgccccgccc | 2640 |
| ccacgtcacg tctccgtccg ctgccacctc cggcccgggc gcacggggaa gacgacgcca | 2700 |
| cacacgctct tccgcgggcc cccccccccc cccaacccccg ctaggtgcta gtagctttt | 2760 |
| tccctctccc atcccatgc agcgccactg ccttccacct ccgccgcaca cgttgtctgc | 2820 |
| gtctgccccc ccattccttc gccttgctcg ctcccgcggg ctaaataata tctcgcgctg | 2880 |
| ctcctcctcc tcggcctcgg ctgccgccac tccactccac tcccctccac gcgcgcactc | 2940 |
| gcttcccgtg ggctgcgcct gcgcgggtga aggagcgcgc gcgcgtacgt gcgggcgggc | 3000 |

<210> SEQ ID NO 12
<211> LENGTH: 3000
<212> TYPE: DNA
<213> ORGANISM: Sorghum bicolor

<400> SEQUENCE: 12

| | |
|---|---|
| tatattctag agtaaatcct aaatatttaa acagctttaa ttaatttaac ccataaacat | 60 |
| atagatttaa cctagatcat cattggtcca cctttagctc taacaatatt tagtcatata | 120 |
| tatctccctc tacaagtttg tagggctaga gagctatgga cacgtcgaaa atatctagtt | 180 |
| aactaatagc tttaatatct tttttaaaat tacacagtac aagtagacaa tcacaacaca | 240 |
| cgtatattta ctcctatgaa ctacacgtac aatataattt atatcattct acaaacttta | 300 |
| aatcatcgtg tattttggag ttttggagac gcgctaaaca tgctaaatat aatcgattgc | 360 |
| ggcggtcatt gaatttctga caccagctct tttgatccta ttgaggtgtt tggcttcaat | 420 |
| tccccttttg atcaatattc atgcatattc atgaggcagg caaaatatag atacatactc | 480 |
| tctgcgttcc aaaattagta tatatctcat ttttctaagt gtgaaaactt ttttgagtgt | 540 |
| gaccaattat atagaatata atattaatat ttgtatctct aaataagttt actacaaaat | 600 |
| tatactctgc taccaatttc ataatatttg ttacgtatta taaatttaat atgtttttat | 660 |
| atatacttaa tcaactttt tttttaaaga atgacttttg agaagtggaa tgtgcactta | 720 |
| taatatttta gaacggaggg agtatacata atatcgtata tattgtgtac atgtggagag | 780 |
| ataaactcaa cttagatgat aagaggacga aatgattgag tgcagcgtgt gttatcggac | 840 |
| agtgaccatg atattcatgc tgagctgaga ctgactctat gtgttttgtg aggtgcgtgt | 900 |
| tgtgttttga tttacaaggt gcaaacaata atgattagtt tcatgctcga tccagcaacc | 960 |
| tgcatatcat tagtagttta ttttttgaga agaagatcat tagtacctta tattaaccac | 1020 |
| gcgaagaatc aaataagtac gtagcaattt gcatgtagca ctgccaccga cctagctaga | 1080 |
| tgttcggcac accttatcat cagatcaagg atcgaaacac tcttgaaaga aaaatgattt | 1140 |
| ggaaaagaaa aattaagagg gaatagatgt aaagcagccg tcaaactatg caggaattct | 1200 |
| gtcctggacc ctagggaatg caacagcaac gtgtacgtat agtcccatct tcccttgtct | 1260 |
| gcaaataatg aaagaattga agaggcaggc gtggaatgta gccgccggcc ggaacctacg | 1320 |
| cacaagcaaa caattttctc ggttacgaaa tattctaacc ggcagagaaa aaaaggaaa | 1380 |
| gagaaaaaaa ggaaatgatg tgcttggcag tgtgtgcagt caaccgaatt cgatcaagat | 1440 |
| atgaacgaaa aacccaattg cacaatttca tccgatattt ctcatctaaa agatcataca | 1500 |
| gctctggtat ccttcaatc tcactcctgg tctccacaaa gatgtaagtc tcgcttctcg | 1560 |
| aatagccatt gctaaaaaaa ttctaaattt aactaggttt atataaaaga aatagcattg | 1620 |

```
gtcaacattt gtatcttcaa gtacgtttat tacgaaaaca gccatttaaa tgaacattct    1680
agatcgaata atggctaaat acaataggcg agaccctgat cagcgtttag tgattttttt    1740
taatgcctag atcagcactg aattttatca tttgatttag aatgtgtgta tttggatcta    1800
taataaatga aacctacata ttgaaaatag tggtatcttg attcgatcta gagatgattt    1860
caaaactcga tctacagcaa aacgtaatgg cgttcgccat gtattgttgt gacgtgaaag    1920
attgtctact acagtaaaaa cttttgtttt ctcccatgta taccagcaga aggtgagcag    1980
gaaggaagga aggaaaatgc actgaacttg gactaccgca taacgcaggt atcatggacc    2040
ataccatgca tgcacatgca gtcatgcacc atcctaatca aattcttcat ccggctccgc    2100
acgagacaaa aatctctcga ttcttccttc ttctctgccg atcgagctgt acaaacgtgt    2160
ttcaccgtga tggcgtcacc agcagtaaaa taaattcact tgccacgtgt cccgccacgt    2220 caccctccc ctcccccgc gagtatataa accctcaccc ccctgcctcc ttcctcccgc    2280 cagttttct ccctcccagt cgagggagca ccattaccaa gtactgtagt ttagtgctac    2340
ttatattacc attactatat tattattact actgacttaa ttaccctcac gcggccagtg    2400
aagccctcta cctttgattg attccgcact tgttgttctt gcgcgcattg cagagagggt    2460
gctctcgatc catctctgca gttttatctc ttaggtaaaa aaaatcaaat cgtgtggtac    2520
caatcaacat gacggtgacg ccgtggatca cggtgagcga cgggacgctg gcggtgcgcg    2580
gccgcacggt gctcaccggc gtgccggaca acgtgtccgc ggcgcacgcc gccggtgccg    2640
gcctcgtcga cggggccttc gtcggcgccc acgccgccga gcccaagagc caccacgtct    2700
tcaccttcgg cacgctccgg tgagtaataa taatattcct aatcacttca tcctctctgc    2760
tctctctatc tacacctatg tcagtgtttc cttctgcgat aagaaatgag gctgattttt    2820
tcatgagaaa cgtctggaat cggaattttc ggttttttt ttttttttg gttgtcgtgt    2880 gttcagtact attttgatgt aacattttg cattgcagat tgttgatgag atcgaaacaa    2940
tgtgtaaatt tctgattttt tttttgtct ctctctcccc cgtggtgccg tgccgtgcag    3000
```

<210> SEQ ID NO 13
<211> LENGTH: 3000
<212> TYPE: DNA
<213> ORGANISM: Sorghum bicolor

<400> SEQUENCE: 13

```
gccacatcag caaaattaca taaataatat gtaattaatt gtcttggact ctgtgataga     60
gtcttgcatt gtgagtgccc taatcgatcc aatgcaactt gctcaagtcg tgggcccgaa    120
aaaatactta cactactaca acggttacac atatggtgtt gcttggcatt tttaagtacc    180
aaatgaccct atttcttgag ttgacgctac caatagaaag acatcatcct tctatgttcc    240
tatatattgt tttcaaaagg gagataggaa tggtttattt tttccttcac attcccatgt    300
gactacgtga gagagcaaga acatcaccag aaacacacaa aacaaaaata tattttttaa    360
aaaatgtagg ggcactaata atggtcacat taatacgagt accaattatt cttgttcgtt    420
tcagcttatt tatcgaattt atcagctatt caacagtgct tttctctcac ataaaatcag    480
cgaacagtac tttcaataat ggcttttcag ccaagcaaac aaaccgagcc gaaagtctc    540 ttatttttcca tgattctata agctaaaaag atataaaact atactttatg aaaaagagac    600
tattaattag cagagatttt ttttctaact ccaaaaagga tacggtttta acaaaactat    660 agtttttta aaaaaaatac aagatttact gtattcaaaa gtccacctgc ttttgagaat    720
```

```
caaagtatta tagtacagta cttcttaaat acttgaaaga tagtagttcg aatcaaacag    780
tggcttaatc tgtgaccgga ccagggcctg tggttttttg caagcaaaag cgacagaacg    840
agagagaaag cccgagagag tgcatgcaaa accagaagcg atgacttggc tcaagtcaac    900
cgcgttcaca aaagactcca cgaataattg aaggccatcc ctttcgtttt ttgggcgcgc    960
cgcacatgac taaaaagcaa aatcagaaat aaagtgggct agagcaaacg atctatgggt   1020
agctaacgca gtataacttt gttggtggaa tcaacgtctt ttacccacag gtagtcagtc   1080
aagccggcta ttttccggg aaaacttatg acctacgacc tacttctacg tctactagaa   1140
gaacgtgagc ctccggaagc gtccagtact tccttggtta aatatctagt ggagtttctg   1200
acagaattaa aactatgcat atccatacgt atctattgat ataggagggg taatacgatc   1260
ttttgtataa ttttctaga ttgagtttga atcttaaatt ctactacatt aatgatatac   1320
atgtatagat gtactatgca taattttaaa tttttagaa ctcctaagta tattttctta   1380
aaagattctt actatttcac caagtaaaag gtttgcgatc aatatttatt cctccttatt   1440
atggttatat gtattttttc caagaatttt ttacttaatc tattctatcc actaggaggc   1500
atactctagt ctgttatgat ttctgctttt gaatgaatca atcaataatc tcgactttaa   1560
gcaaatagat aagaatgata atatttctat gtaaatttag aagaaatagt ctgttatgat   1620
gcatactaaa tattattaaa tatgttttc taaatttgga tacagagtta ttgataccat   1680
ttcttctaaa tttacataga cttattaaag tttaacttag ttcaaaccta agatttttt   1740
agataggggt acttctagta tgctttaatt ttgtgtgcgc acaagtatgc caatttcatc   1800
aaccttaagg ccaccctaga tttcttgagg ttagtttgta cattataaca tttagttaag   1860
ccaaaaaatc ctatggccgt gtccaaggct taagatcgca agctcaaggt gaatctatat   1920
actgacgttg ccatggtctc atcttttcc ttgcaccact tgttctgcaa aaagctcaat   1980
taacatcggc aagcacatac tgtggcgcat cgagaagaac ttacccaatg catcagatcc   2040
tccatcctcc gccgagccct ctatggccaa ttcctcctag ctgtctgctc ctccatcttc   2100
gtcttcccca cagccgggca tcgagctgcg agctccagcg tgagatccaa caaggcacgc   2160
ggccccttcg cacggacgag caccggcagt gtcttgagca cgacccctc gaggtgcggc   2220
cccttcgtct gtcgttgtcc gagatccgtc cctccccca ccttcttcaa cgacagcgcc   2280
tccatcctca ccgtgagcgg tcctctcctc cctcgtcgg cagagcagca ccggcggcgt   2340
ggccctgcgg ttcgccggag tggccctgcg cttgtcctcg ctgcgggagt tgaactcgtt   2400
gaagccgcgc cactagcgcc caaggccgcc gccagcgctc tgcgcccctg ctcccttcac   2460
tctctctctc tctctgttcg acgttgtgtg gagacgcaaa caaatcgaga gaagaggcaa   2520
ttttgccttc tgtgttgccc accacctaaa atggattctg tgtttgcata gtccgttaga   2580
gcctgttttg ttacgataaa acactgtaga tgacgcattt tttgctatgc gtcgtgctct   2640
gcctactctg ttggagacag tcttactgtc ttacacaccg gaattggaac aaggcaccga   2700
gcgcgcgctc ttcgttttgt ttggttgcat tgcagcacgc gctaatcccc gacgcggtca   2760
atcaaacccc ccacgaggcc acgacacgaa caccagggag aaaggagagg agaatgacgc   2820
gcacagtgac ggtaggctgc tgacgctgtg atccgtgacg atactactat acagcgcgtg   2880
gctcctcgta tcgcgaccgg tcacggcgcg tcggtctcgc gctccacttt ttccactcag   2940
ttgcgtcaca attttcacga cgccgcggcc ccccggcacg ttcgatcctc ccgagtcctg   3000
```

<210> SEQ ID NO 14
<211> LENGTH: 3000

```
<212> TYPE: DNA
<213> ORGANISM: Sorghum bicolor

<400> SEQUENCE: 14
gaagctgttt tggaaataag tgtttgacaa agctcataac agctcatgaa gctgttgtga      60
gctgtaccaa acaggaccta aataaataaa gaaacaatat agggagtttt cacaaggctc     120
tcgatcgcgc gagagaaacc ccggccccaa acccaacata aatcccagtc ctctatttcc     180
caagaaaaca cacagaaatg tcacctgaaa tcaagtatct tggacgcacg ctccatcgtg     240
gcatgccatg tcacacccca ctccgcgagt gcggcggtcc tgagaggcgc tggccgctcg     300
ccaactcacg atccatggag gcaaaaagca agcgaggacg ccatcaaatc gccagctaga     360
tcgccggtgg tggggcgcac acggcagcac cacgcgggca cccttccccc tgaaacggac     420
cgccgatctc gtgacagaga gatcggggcc gcgccgggaa cttgcgtggc gtcgggccgt     480
cggggaaaaa tctcgccgga acggaacaac caactggtgg cgccggcgca gcgtgtggcc     540
cgcgcacgtg cccgcggatc gcaaccaacg gtgggcagcg ctcccgggcc gcggccccgc     600
gcgcgtcgcg acgcccggcc ggcgacctgc cacgcgggc cgcgggcgcc ctcagccgtg     660
aaacgcgtat cgcgccaccg tgtgtggggg ccccggccgg cccgcggcgg cgacagcgga     720
tcgacggtca cgagtagagg aggaggccgc gggacgagcc gacagggag ggcccgcggt     780
ctggttgggc ggacgacggg gacacgcggg cgcgcgcgcg tcgtccgttt cgatcgccgg     840
cggtccggcg agcgagccag gagtgacggc gagtgcggcc aaaagctttg ccttgccgga     900
ggcgaaatga aacggtgaca gctagatcac gaggcagcgc gttttgatcg cgtcgcgtcc     960
tctcggtcct cagatgagtt gccaattaag ttctggtggc ggttgcccag cgccgccggc    1020
gatcgctgtt gacaagtctg accggcaggc ggcggcgcgc gagggccgtc cagattagga    1080
gggaggtttg tactcttgcg ggcattgtca ttttctttg aaaaagctga tgtatactac    1140
gtttccttt tgaaacgact gatttgtaca tttctttttt cgatttatac atctgaggct    1200
cgacatttta gatatcacaa gataaatatc tttttatata gtgtgttttt aagcgcggca    1260
attggctgtg aatttatttg ttatagattt ggacaacatg attcatagtc attgccttgc    1320
ctaagtggtg agagttaagt ggtgagagtt gaatacttga caattgacgt aataataata    1380
ataataataa taataataat aataataata ataataataa taataataat aataataata    1440
ataataataa taataataat aataataata ataataataa taataataat aataataata    1500
ataataataa taataataat aataattaat tattgtttgt tccagttttg atcatatgtt    1560
aaatgatggc gtcttgtttt tctcaaacaa gaaacaagac caataacagt aatactacgt    1620
atatagtttt atgtttgtat atactttgtt ttatggttga attatcttca aactagttag    1680
ctagcaccta tatactcgta caagtctaac acatgtccaa gccctaaaaa agaaagaaag    1740
tctcaatatg tttctcttgg tcaccagacg atcatagaag tggtgccccg tgatgaaaaa    1800
aaatccagga atattctttt gtcaatttta gccttgcaaa attcttagta aactgtgttc    1860
agacttgtca taactcaaag tctacatcac aaacaagcgg acaaaaaacg tagtaatcta    1920
tcatcgttgt gaaatgaaaa aaaagtgtg gagcacaatt tcaactaaat gtattgtagc    1980
agaaagaaac attgtatgtg tacaaaatac gaaagaattt tgtacaggca gtactaaaaa    2040
tcgataaaat ggcatttaaa attcaaattg tttccttaaa agaaatatgc attattgtgt    2100
tcatgatatt gtcaacatta aagaggtata ttgccaattt gccatgaaac ttaatgacat    2160
attgttcaca tactctgcac cacacacttt gtggttattc cctaattgag tcaaatcata    2220
```

| | |
|---|---:|
| tatatgatac ttccaattct ctatatacga cattataggt gtcaatgtgg tttattcatg | 2280 |
| ttctatatat ctatactaat ataagcatga cactttctcc tattgattca tttattaaat | 2340 |
| taaagtttgg cacatataaa gcataagaca gtgaatatgc tcagatataa gtcaagcgag | 2400 |
| tgtaataact gaacaacaaa taataatatc aaagaaaaa caaaacacga aaaacccact | 2460 |
| gaaaccataa aaacctcatg gcaaatataa aaaataaaaa atctgagaaa gaagcaaaac | 2520 |
| acagatccaa attgccaaac cgccttcctt ctccttcgcg cgctgtctat aaataccttc | 2580 |
| catctcacca ttcccttccc atcagagatc agacaagagc agacagccac acaccacacg | 2640 |
| cacagcctcc gcagctgcag gcgcctgctg ctctccgacg agaccccaag aactcgccaa | 2700 |
| cctaggccag ccacccttct tcccctctgc cgcaatgaca atgctggtcg ccgccgcctc | 2760 |
| cgtcaagccc tccaccaccg cggctgcggg cacctgcaag gcgcccttca gcccctccg | 2820 |
| cctccctccc ctccccgccg ccgccggcct caggccgctc tccctcgccg tctccgcgcg | 2880 |
| tccgctgtac cgccaggagc atgtcctctc aaccgtggcg gtggcggcgg cggcgggccg | 2940 |
| caacgaccgc gccacgtccc ccgcgccgcc gtccgccacc gcggacggcg cccggccggt | 3000 |

<210> SEQ ID NO 15
<211> LENGTH: 3000
<212> TYPE: DNA
<213> ORGANISM: Sorghum bicolor

<400> SEQUENCE: 15

| | |
|---|---:|
| ttcatgctac atgcatgctg gttgatttgg ggcattagca gctcaacatg tactcttgtt | 60 |
| ggcaggaaaa aggacttata attccaaaga atgcaagcag agtggaacaa tttgaaaaga | 120 |
| attctggtac tagaaaccat tgcaacaact tggttgatgt tatggacaca caaaatgtag | 180 |
| caccacctag gcaaaaggaa ctaccggtgt caagtaccgc tcctggctct gttcttgata | 240 |
| aaccatgtgc gtgtttgtct cagttgtttt gttttgtttt gttttgtttt gttttcaac | 300 |
| ctatatattt gtcagatcaa tgtctatgca tatcttcaca ttagtttaat cattcatctt | 360 |
| atttgtgcag tggttgtgaa ggttaagttg agtaaaggag gacctcgtgt atcgttgtat | 420 |
| gagtcgtgta aaaagcttca gtggccaatg cctatgtttg aatttgtgaa agtcgagcca | 480 |
| aggtactact gtttcacatt gtgtttgctg ttggtttgtg taaacaacta cctaatcttt | 540 |
| tcacttttga aaatatcagt gtgtgctcct cttccggtga ttcttcacaa aaggttgcac | 600 |
| cccaaggata tgcatttgct tcaacaataa cattgcatat accgaacggc gatatcatca | 660 |
| gcctcacagg agacggacgt gcggataaga agagctcaca ggattctgct gcgctgctca | 720 |
| tgctctatga gctgcagcgg cgaggtagat tccaagtcca agaagtatga cgaatcacaa | 780 |
| cagattcatg gttccatcac caaggtgta atgttacctc cgattattgc ttgggcatct | 840 |
| tggaataatg tcatcaccag accagttgcc cttagttggc tgctgcgatg taggaaaata | 900 |
| atgtagccgt gtaggttact cttgttcttg ccttgtgatg aatcagacat ttcatctgta | 960 |
| tatatatagg cgcatgccaa taagagccgt ggtcatgatg tgtgtacaca tgcagtaata | 1020 |
| aagcatcaca tggtttccag actcgggaaa aatctatgag ctgaaattgt caccaaaagc | 1080 |
| aatatgctta catgctgatt ttaacaggaa attgcgaatc ttcacggtac actcttatcc | 1140 |
| atatatttgc ccgtgctctg caaacagctt ttcctatggc agtattctcc tcttccaggt | 1200 |
| tatcaaacta tctttatgat gtaagaacga aatcattata caaaatagca atgagcacag | 1260 |
| gggatcaggt tatgatgatt tactcgacct tgtaaattaa aaggtcaact tgactacttg | 1320 |
| agagcagcgg tgagggctgg tgtctgatcc acacgatgga gacacacaac acaaacttgc | 1380 |

-continued

```
ccttggcagt cagctcagca tagatatcaa ggactgactt ggtgaaccgt gcgctctact     1440
cacagtggat gatcacgctg gtaaagcaat gtagcccacg attggtgttg aaaggtttgc     1500
tgttgatgtt agcaacaagg aaaatggcaa aaacatgcag aatacgtgaa attggccgtc     1560
ttgttagtga tgccattgaa atggagatgg caaaagaact atggctcaca attggtagtt     1620
taaaggtctg ctcttgatgt tagcaacaag gaaaatggta aaacatgaag aatgcgtgaa     1680
ttttctctct ctcaagatct gttgacactt gaatgaatta atataagaag ggaagcaaca     1740
caaatacaag aggcagttcg tgccaggagc acgatctgca ttacatgagg ctttcagatt     1800
actctgaggt ctgagctacg cgccacccct gaattgtttc ttctgtaact gcctagcctc     1860
cttacataca tggctgcatg aagcctcagc ctttacattg caacctttac tgcatgcatt     1920
cagtttgtga gtctgaatct gaactgaaac aaacaggctt tcattttggt tccaagtgaa     1980
acgtggtgtt ctgatctgca gcgaatgggg ccatggctag tttgttacag gttttagcag     2040
ctctcacagg gctgcagagt agcttgggac ggcgcacaaa caggctttat ttagtagtaa     2100
atatttggag tacaatctgt tggatcccaa gattcttagt actgagaact gaaactcaaa     2160 tatttttct tctcttttg aaatgcagta tataggtata gcattgaatt tttgtcagcc     2220
aactgtaatg aaatagtgca gccgaacaca gtggttggtt gtcacaaggc ggcatgccct     2280
caccctccta tctattggat tcgttttgtt ttgagaaata tgcaaacaca cacttctcaa     2340
aacgaatcta ataagtgaga gtgagggcat atactctcaa gagtaaaata aactttacct     2400
tgattgtcag gggcgcttgg cactttggca gcgaatgatg tactccttaa gttgagatcg     2460
caataattgt acatgctgct aggccaattc aaatttctcc aaagcgatgc aaccttttt     2520 tttaggataa catgacacca tttgaatgga agttgtgctt ctagcaggtc ttcaaacacg     2580
cctaggcatc gcggataaac aacataaggc tttgtttgga tgttgtcgga ttcacctcaa     2640
tccacatgtg ttggagtgga ttgagttgga atttagttca agtttcactt caatccaccc     2700
caacgcatat agattgatgc gaatccgatt acatccaaac aaagcctaag ttggaccttg     2760
ggcccagcat aggctgggct gggcgcccaa gccctagttg aagaactccg tgacccttt     2820 ctcattttgc tcctcttgtg agctctccgg ttcaaaaaca caggtggcaa aagccgcaac     2880
aatattatgg aaaaaaaaac gcccataacg aagggggcag atccccaggt cacgaatcgg     2940
acggtccaga cgatccgtcc accctttaag agcggcccct cccgttatt ccctctcccc      3000
```

<210> SEQ ID NO 16
<211> LENGTH: 3000
<212> TYPE: DNA
<213> ORGANISM: Sorghum bicolor

<400> SEQUENCE: 16

```
atgcgtacgt agtactccta cgtgcaccgc cggagacggc ggcttccac ggcgcttttc       60 taaccgataa cgtcgccgtc ccgaccggtc gaatccacgc gccccgggt ccctctccct     120 ccgcctgcag gtcgcaagcc cgctgccaca tctgcacacc accgcgatcc agcggcttcc     180
agcagcagca gggtatcctc ggcccggggcg ccctggcccc tacaccctac tcctacacgg     240
cacggatcca cagctgcact gacacaaaga catcgcatct gaccatctgt tctcccctcc     300
cgcccggtca ctgcttaaac gacccgtttt tgatagggct tgttttcata aaaatttatc     360
caaagattcg atgtaggaag taacagaaaa tcttaaaatt tattttaaa actaaactag     420 gcctaaacat gatcatacga tcagttataa gttaaaccgg tctctacgtc agaggtcagg     480
```

```
caggcactct cgcaatgatt ccacgggacg ttttggccct ccctcttttg ccgggagata    540
aggcgatgat gatgagcggg cttccccgcc aggccgccac cctcccagtc cctttgctgt    600
tttcctccga ggccatgatt gtcccgggat gtcttgcgtc gcgcatactt cttagatctc    660 gctgccccccc cgcaacttt gcaggagatc gagccttgca ttgcacacac attgcagtgc    720
tgcggccggt tctcagctcc ggcctttcgg tcattttcag cgctcgcgcg ctcatgagag    780
catcgcatcg catccaatct cctaggcctt gtttatttcc aaaaaatttt gcaaaataaa    840
aataataaca cttttatttg tatttgacaa atattgtcca attatggact atttaggctt    900
aaaagattcg tctcgtcaat ttcgaccaaa ctgtgtaatt agttttatt ttcatttata    960 tttaatattc catgcatacg tctaaagatt cgatgtgatg aagaatctga aaaattttgc   1020 aaaattttg gaaactaggc cttgtttagt tcctaaaaaa ttttgcaaaa ttttcaggt    1080 tctccgtcac atcgaatctt tagacatatg cataaagtat taaatataga caaaataaa    1140 aactaattgc acagtttggt cgaaattgac gagacgaatt tttaagccta gttagtccat   1200
aattggacaa tatttgtcaa atacaaacga aagagctaca atatcaattt tgtaaaatat   1260
tttggaacta acaaggcct taacaagccc ctattcgatt ctcctccccg tgcccgcatt    1320
caattcaaat gggggtgggt tcccctgatc tgaggatctc accgtacgtc acgccgctcg   1380
cagcagttgc atcgcaacgt ggaattgaaa tgacacccgg attctctcca atgttaggcc   1440
ttgtttactt accagaaaaa tttgcaaaat ttttcacatt cctcgtcaca tcgaatcttt   1500
agacgcatgc atggaatatt aaatatagac gaaaataaaa actaattaca cagtttggtc   1560
gaaattgacg agacgaatct tttgagtcta gttagtccat gattggacaa tatttgtcaa   1620
atacaaacga aagtgctaca gtgtccattt cccaaaattt ttcggaacta acaaggcct    1680 tacgactagt aaaatctgac acccggattc tctccaatgt tacgactagt aaaatctgac   1740
caaggtcttg tttagatgcg aaatttttt tggtttcact agtatagcac ttttgtttgt    1800
ttgtgataaa tattatccaa ttaaagacta actatgataa aaagattcgt ctcacgattt   1860
acagataaac tgtgtaatta gtttttattt tcttttatat ttatatttaa tgcttatgca   1920
tgtgtcgaaa gatttgatgt gacaggaaat tttaaaaact ttttggtttt cggggtgaac   1980
taaaccaggt ccaaataaag ttaaagaaaa ggaaatgcat tgcatggtgc tcggaactgc   2040
ctttgacgag cgtcaattga ttcgggtagc acaacacgga atctaaggcc ttgtttagtt   2100
tcgaaaagtg aaaagttttc ggtaccgtag cactttcgtt tgtttgtgac aaacattatt   2160
caatcatgga ctaactatga gcaaaagatt cgtctcgtga tttacagcta aattatataa   2220
ttagtttttg tttttatcta tatttaatgt ttcatgcatg tgccataaga tacgatgtga   2280
ggagaaatct tgaaaccctt ttggttttca gcgtgaaggg cctgtttaga ttgggaacga   2340 aattttttg tgtgtcacat cggatgtgtc ggaaggatgt cggtagggat ttttaaaaac   2400
taataaaaaa acaaattaca tagctcgtca ggaaactgca agacaaattt attaagcata   2460
attaatctgt cattagcata tgtgggttac tgtagcactt aaggctaatc atgaagtaac   2520
taggcttaaa agattcgtct cgcgattctt aactaaactg tgtaattagt ttatttttt    2580 atctacattt aatgttccat gcatgtgtcc aaagattaca tgggatggat gaaaaaaatt   2640
ttggtaggaa ctaaacaggg cgtcctatag cacaccgaaa tggccacgag aaaaaaaac    2700 acagaagaca actgttggcc ttgcccatgt catcagcgag tgctttctcc agctcactac   2760
tgacgcaaaa aagaaaaga aaaagtttg cagctgtagt agactcggtc ctccactcct    2820
ccagctctcg gctcggttcg gttcgcgcga aaccctaacc accggagggc ggtaagggag   2880
```

| | |
|---|---|
| aaaaatcccc aaactccccg ccctccctcc ccctacctct caccgcgtcg ctttcgccgg | 2940 |
| acaccaccac ctgccgcttt ccctctccc ttcgccgccc atctcctccg cccctttttg | 3000 |

<210> SEQ ID NO 17
<211> LENGTH: 3000
<212> TYPE: DNA
<213> ORGANISM: Sorghum bicolor

<400> SEQUENCE: 17

| | |
|---|---|
| ccccgcaggc gcaccagcca ccatgttgcc catgaaaaaa aaattcttgg ccggagccta | 60 |
| gcccgacata ttattttagc taattttata gtgtaaaaca tgcaaacagc tcgcccaagt | 120 |
| cttagcctaa cctgccggca taaaaaaata gttccgactt gcctagtggg actgtcatgg | 180 |
| acgaggcttt tttggtccga ataactgga ttttttcgg tccggtccaa accgcaaaat | 240 |
| gctcaggtct acctgttgac gtcccacaac tcttgcaaag ctgaagccaa ccactatgga | 300 |
| ggagaagtgt gtgcccctgc tcgatctatc cctgacccat gcagtttacg tgtggccgga | 360 |
| cgagcaggag gaggaagata agatgagggc aacatggtct ttttctaggt ttttagggat | 420 |
| tttgatttct tttagttcat ttatttcatg tccacttagc atacatctaa aatagggata | 480 |
| aatggatggt tcgtttcaaa ataacaaaga aaaaatcata aagttgaaaa aacatgggca | 540 |
| aaatcacaat tagactacag gataagggca agaacacaat tttccaaaaa aaattatatg | 600 |
| caaaaataaa aatcgatcac acatcataag aagttaaaac gcttaaaaca taaatggatc | 660 |
| tagtcggcgt gattatgcaa aaactagtct aaccggttat aaggccgagt tgtaaacata | 720 |
| gtgaaaaatg ataatatttt cgagcaaatt agcaaaaggt aaccaacagt cttacatggc | 780 |
| gaaaagaatg actaatttct aggtaaatag taaggagac gtcgaacctc tcgtcggagt | 840 |
| aacaatgttg gcagattatc gctcaacaag cctagagcat catctttgat cattgctatt | 900 |
| ttttatcgcc agattaagcg atgaacaata atatagaggt tggagaagat taggacaaaa | 960 |
| gagaggtata gaatagtttt attctatagg ttgaatatct tattttata gagtagtcct | 1020 |
| ctggtatata tagataggat aatcttattt tagtaggaaa cttctctcaa atgaaatctt | 1080 |
| cagttttccc acgagattgg acgagttcct attgaattag atttgaatgt gactcgggct | 1140 |
| gtgaaaacca ccttagaatg tttgtgaaac ctaggcttaa cttaattaag taatagcata | 1200 |
| agtgttaatt tatataaaat tttagaaggt atttagatta tctatcatag tagcaagtag | 1260 |
| agtagtacat ataagagag ttactttata atgtatttca ccatttagat tacctcagca | 1320 |
| tgcaccatgg tccatggaac tcaaaatgat gaatttgtcg ttgtaacaaa gaattgtaat | 1380 |
| ccctctgatc cagtttataa ggcagacata catattaaga ttcaaacttt acgatctttg | 1440 |
| accaatattt ttaataaaaa cttgatatgg ttagattcgt aaacaaatgt tctatccaat | 1500 |
| tatcatagtt tataatcata aaaatataat ataaaaataa atggtcaaat gcaatttgac | 1560 |
| agactatgtc atgtcagact aggccttata aaattaacag gatggagtat gtctaatagt | 1620 |
| atcctttat aaagaacata gagcggtaaa acttaattag tgttatatga cataatgttt | 1680 |
| caatcactgt ataaacttat ttaaaataac aaattatatt ttattatcat ggagtgacta | 1740 |
| aagcgaatta tcaatgtctt tgatatattt attaaaggag gtcttattta caccatgcag | 1800 |
| aatttctcgt taagacgatc agagaagtct tgagagtctc actgatcaga gattgcaaac | 1860 |
| accttggcaa tttaaagctt acattgaact ctttccagac tccctactgt ttcagttcag | 1920 |
| ccaacagtag acttttttatt ctacttctca acctgtatgg atccaacagt tggtgcatat | 1980 |

```
atatcagcaa caatttttc caaaaaaaaa aaaaaaacat atcagcaaca cacagctaca    2040
accaaactat tctgttcttt agctatgtcc agccctcggg gtcacttcac agttcacact    2100
gcaataaagt agatggctca aagcagcgcc ttctcttgct ccaagcgcac ccacctgacg    2160
taaacaatgc gcagagcaag atttacattt acatggagtc acagcagcag aagatagga    2220
tttaggaaaa ggtcgccggc aaggcaaggc aaggcaaccc aagtacccaa ctgcaactcc    2280
gaggctccaa acttgtgagc acaccagcgg cggcaatggc aacatctgaa acgacgcctc    2340
tgctcttgag ctcgtcttgt ccccagcctt ggcgcaggcc ctagctatca acgttggagc    2400
ctcgtcagac tcaccattga ccagctcata ctgccagcca gcatgacgtt gactcgttct    2460
cgcttgcctc gtcacagctg attgcaccgt ataaagcct tgtttaggcc ttgtttagtt    2520
ctcagaaaat tttgcaaaat ttttcacatt ttccgtcaca tcgaatcttt agacgcatgc    2580
atggagtatt aaatataaac aaaaataaaa actaattaca cagtttggtc ggaattgaca    2640
agatgaatct tttgagccta gttagttcat gattggacaa aatttgtcaa atacaaacga    2700
aagtgctaca gtgtcgattt ctcaaaaaaa ttcggaacta acaaggcct  taattcaccc    2760
caaaaaccaa aaacttttca agttgcggca cgtgcatgga gcattaaata tagtaaaaaa    2820
aaataattac acaatttgtc tgtaaatcgc gagatgaatc ttttgagtct agttagttca    2880
taattggaca atatttgcca caaacaaaag aaagtgctat agtgtccgaa aacttttcat    2940
tttgccaact aaacaaggcc ataatataag agagaatgcc ctgctgctca cggctcagtt    3000

<210> SEQ ID NO 18
<211> LENGTH: 3000
<212> TYPE: DNA
<213> ORGANISM: Sorghum bicolor

<400> SEQUENCE: 18
ggcacagcga ccagagagtt cggtgggatc atagtaaaca ttagggcact cacaatgcaa      60
gactctatca cagagtccaa gacacttaat tacatattat ttatggtatt ttgctgatgt     120
ggcagcatat ttattgaaga aagaggtaga aaaaataaga ctccaagtct tatttagact     180
ccaagtccac attgttcgag gtaataaata gatttagact ctatgataga gtctcacaat     240
acagactcta tcatagagtc taaagttatt tattacctcg aacaatgtgg atttggagtc     300
ttatttttc tacctcttca ttcaataaat atgctgccac atcagcaaaa taccataaat     360
aatatgtaat taattgtatt ggactctgtg atagagtctt gcattgtgag tgcccttaca     420
gattaattat tttgctccag cattgatcct ttgcatgcat gtattgaact ttggaaaggt     480
ttgcgtagct catcttttt aaccccgccg gttatgcgta gctcatacga gtattttgat     540
agccagcact agcatcagca aaagctata  cgattgatg  caaacacact gtgccacaat     600
atgattgaat aacaaagcac tttgcgcgct cacgcacgaa agtaatacca ggtaccgcat     660
gcgtgttcta atactagcgg gcacactatc actgatgctc cttattaccc tgaaaaattt     720
tcaccgatgc tctttaatat tccttaacac ataagcaatg caacttacag ccctgccagc     780
tgccacggta caatacgcac atagtactaa ggctctgttt agatgccaat ttttttttatt    840
ttgctactgt agcactttcg tttgtttgtg acaaatattg tccaatcata gactaattag     900
gatcaaaaga ttcatcttgt gatttacagg aaaactgtgt aattagtttt tgttttcgtc     960
tatatttaat acttcatgca tgtgccacaa gattcgatgt gacggggaat cttgaaaact    1020
ttttggtttt caggtgaact aaacaagacc taattgaaaa tgacacatac tgtttctagc    1080
atttccctgc aggtaaggcc ttgtttagtt caccccaaaa agcaaaaagt tttcaagatt    1140
```

```
ctccgtcaca tcgaatcttg cggcacatgc atgaaccatt aaatatagac gaaagcaaaa    1200
actaattaca cagtttagct agaaatcgcg agacgaatct tttgatctta gttagtccat    1260
aattgaataa tattaaagtg ctacagtacc gaaatccgaa atcttttcgg aactaaacga    1320
ggcctaaaat tattggctat acgcgtcgtg gtcagttttt aatgttatct catcagacgt    1380
gacgccatgc tccaagagaa gcaaccaggg catctgaatc taatcacagt agaatatttg    1440
tactgtgggt tgggtagatc attaatttgc cgagaaaaat gcagtggcca cttgtccccg    1500
atccccgggc atgtacgtcg acctgaaact tagtcaaaat ttcacaattc atggttcagg    1560
taccacagta tcagccgctt gttaattagt gtaatttgtt cttgtttgtc tgatgtttgc    1620
tctatgctgc ttcgcagaag ccagaaggta aagcggccaa tctgtgcttc tggtcggcgg    1680
actaggcgcc aagtcatcat cgatggaagc ctcgtgtgtt tccttgttct tcattcaatt    1740
accgttggcc actcgggcgc tttgaaggac tgcaacgtgc atttgttgtg acgcagcaag    1800
ccgtctacaa gtcaagacaa aaggagcaaa attaaagaac acctcagcaa ctgtaaagaa    1860
tcaatgtccc ccgtgatgct tgcattgatg cttctatctg ctgccattgc atggagttgt    1920
ttaatttccc tccgatggtt aagttgtgta tagtattacc tagggttgga aaacttcatc    1980
agatcttttg atcccaagtt aaatatctca aatatgcttg cgtcatgagt gacaatattg    2040
atagaataga aacccgccag ttttttgtatt ggtgtgcttg ggaagtttca ggcatagttc    2100
tttggcatct ttggaaattt cacttccccc gtagcagacc agctgtccag ctgtacggtt    2160
aaaacaatat acaaacctaa acatttcac ctgaccccaa tggagatgct tacgatcgtt     2220
ggcaatacgc aatacgaaca aaagatcagg tcccttgttt aatcaggcta gttggtgcac    2280
acgcaattgc acgagctgac taatattact gtattagtta gtgcatataa tacgtcgtca    2340
gttccctccc tccggtcctt aaatcttcgc cctccgccac cctcaggcca cccttctgc    2400 cttcacaaat cttcttcctc tcgtccctag ttgagtagag gcactgcaga gcacacagct    2460 cttggttgt ttgggaagtg cagccccatg cctcctcctc ctcctcctcc tcctctcctc     2520
cggatgcctc acttcagcta gctagctagc taagttcctt cctgcttgtt tcgtgttcat    2580
ccgccaatct ccgtgccatg tcgctcacgg aggtcagcct ccacttctgc tacctccact    2640
ccctctccat cgtgcttctc tacttcttct acgtcatctc ctgaatcggc cgcctctcgc    2700
caagttccga tcgaacaaag ctaagctttg gtttgattca gagccgaagc tttgttcgtt    2760
ccaaacaaaa aattactact attgattact cctccatgct tgttcctctt cgttcttcca    2820
tgatgacccg ttcacgttca tctcccgggc tctctttgct ttgctgctaa gttccgtgcc    2880
tctcctagcg cgcgcgtact cctacactca gatcgatcat tcgactagga gcagtgcgcg    2940 cttttttggca gtgtttgaag cagttaagta cgtgcttccc ttctgaaagt agtagctagg   3000
```

<210> SEQ ID NO 19
<211> LENGTH: 3000
<212> TYPE: DNA
<213> ORGANISM: Sorghum bicolor

<400> SEQUENCE: 19

```
catgggtaac tataactggc attggaaaca ggagcatatt tacaatcgta acaataattt      60
aattgtgcta acagtttgat ttcatatcac acaaatgttg atttcatatc atgcaccgaa     120
acaaacacaa taaaaatcac ggtttactcc ctagtccctc ggtggcgtgt ggtccaatgc     180
aaagtcaaga agtgtggcac gtacgaaata gagtggttga gatataccag taccacagta     240
```

```
gaaaagaaca ctggtacaca caaatgtcac tgatctgaat gtgtaaacaa acttttgttt    300
gagttagtca tgcactgtgt aatcatcaac agcttgaaga tttggatttg catgccaact    360
ggccgtatga aaaggaccca tcgcagctag agtacgtgta acccttgtgt aaataaaaat    420
cacctggaaa gcgccactat tgaacaagac gacattttt gtttactgac ctcatactgc     480
ggggaatacg aatatccaac caaatcagtg aagtgtcaaa aagaaaacgg ccactcagct    540
tggattgaac aagtgtttct attgaagcac attttaaatt gacaacaaga aaaacaagga    600
tatattttaa tcaattttca aatactgatg cggagaattt aagtagaatg cacatctaca    660
tttctatatg ggaactgcat cgttggtcgt ctcgctgaaa tttggtttat gctaaaaaat    720
attctcgcta aaaaatattg tttaagtagt gcagtgaatt tttaaggtca gtcccaatgg    780
agtttcaata gagtttatg gacattaaat atgctgatgt gacatcatat taatgaagag     840
atagatgata agagctttat gtgagtagaa agagtttcat gagaataaac tcttctgtac    900
agtttccaaa atataaatac gttgaaggtt ggcctaacac ggcttacaca cgaacaaaag    960
cattgagata ctactaggaa ccacacgatg ctagtaagac aatgggcaac ggcatatgaa   1020
caaatgtgcc tccctgaata tgtgaagaaa ccttttgtac ttattagtcc agcactatga   1080
aatccaccgt tttgaatctt ggacttgccc gccctggct ggacctaact atcaaaggac     1140
ccgttccagc caatcctagt cctcctacta cactacactc gtagtaaagc agaatcagcc   1200
ggaaattgtc ttgcttcct ttggctttgg tttctccaac tggccacagg tgagacaacg     1260
ccccattctg tcttttgttt actcaatcca catatggtag ggatttcttc cttgacacac   1320
acgcccggga aacccaaat ccgtcattac tcgtcaatca ctacccgaca ttacgccgcg     1380
cgattcctcc gtaatgacca ctcgaagatt tggacaggta gagaccacag acgtcctcca   1440
ggatcagacg tcaggatctc acgcctcggc atctcgttta ttacgcagtt cattacagcc   1500
acggaaggtt cggccgacgg ccggccatcg ctccaacggc accgacgcga gtagtgcata   1560
gaatagcgtt cgcaaattgg ctgcaaaagg aggcgctgat cgagcgagca ccggcgatct   1620
ggcatggcaa agctccccgt cgctcaatta cgccgcgacg agacgagacg acgagacgag   1680
acctttacgt ggatctgctg gtggccacgg atcgggcagc cagctcgcag gtgagccgcg   1740
tccgcgcctc ctgcccgtgc ccgtgccggt gtggtggcca ttaggctgtc cggtttcggt   1800
tgttcggcgg cgacgtgtga cgggaccttt gtgcgccaca ttaacggcgg cccgcggggg   1860
tcatgcggca cagcggtggc actgggcgcc gctttcggct cttttattat ggcggggcg    1920 cggagcgaca cggccctggg ttcgggttcc atccatcgca tcccatctac ctgccgcttc   1980
tcggtggctt ccgcaaagtc gttgaagtgg tcggcggcga gatcgcaacg gcccaggtga   2040
cgtcgctttt gagttttgac gcgagaactg gaccactgct tcttatttgg tcctgtctcg   2100
tgtcacgatc ggagccgtga cacggtctct cctggtaatg tcgagtgcta tgcagtccag   2160
tgcaggcacg agtcatggct gcgcgacttc tgctcaggtt cacaacttca gctcttgtcg   2220
acgtcgtcgt ccgtcacgga gcccgttttt tgaaaaaaaa ataatagagt tgtccgtcac   2280
ggaattggcc gtgtagttag tctctgtctc ttccgccagc ggcagcattg ggccgttgac   2340
ggttggtttt tgtgtcgagg acgccattga cgaacgatac gttctgtctg gttgattgat   2400
ggccgagagg gacggcccag tagcattgat aggctgcggc ctgcgtgggc tgatgatcgg   2460
gcctagtggc gacaagggca ggcatcctga gtcctgacgg atgcgagacg gcccgtaaac   2520
aaggactata tagtaggcct aaaagcgaaa gcatgtcgcc acaaattgtc tcagatcggt   2580
cggtcgcaca caagcaagac acaaattgtc tcagatcggt cggtcgcaca caagcaagac   2640
```

```
tgggcacgac ctcttcaaaa cccacgacca ccgagcgacg catctctctc tacgacgtgg    2700
acacatggta aacgtgtgca gctatccaag aaacgatcat cgtttctaga gctataatgc    2760
tcatcagaga cttcgtaatc aatcgctttg cttatccaaa agactctgaa atggcggctc    2820
tctgcgcaca aaagttcctc gcattttgtt tagaaaattg caagttgaga tcaagttttt    2880
ggacaaaaac agaaccggaa ccggcaggtc tcgcgattca aacgcacgag cgcatgtgtg    2940
tagcaggcgg gatatatacg ccaccagtca tctcacagat cgtttccact ttccaagtca    3000

<210> SEQ ID NO 20
<211> LENGTH: 3000
<212> TYPE: DNA
<213> ORGANISM: Sorghum bicolor

<400> SEQUENCE: 20
gcactgctga tgctggcact ggcaggtctg aggcatcgct tcttctggac tctcttctct      60
ggtctctgga cgggtgcatt gagggagacc tgccggggat catggatcat catcaatcat     120 caggggact cgtgcatggt ggaggcgtca gcgcgtggac ggtggagccg tggaggcgta      180
gcgcaggtac tctctgactc tgaagagaag aggcgcgatc tgctgcatgg ttgcctgaat     240
ttgtggtgga ctggtgggga cgagcatgt ctgccgtctg cgtcccggga ttatgattcc     300
tcgtctcttt cctagtttcc ttgcatccat ctgtgtggcc gcctgatgcc tatcatgcga     360
tggccggcat cggcattggc tggggccctg ggggtccgg cggcggggtc gctgggagcc     420
tggcctgtgg ggacacgact cattgacacc tgactacctg tgtgaaactg actggtacga     480
gtatgccagt gcgacgcatt ttacagtaca catgattatt gcctgggacg aacaaactga     540
ggcctggttt aatgccttgt ttagttctag attttttggt atttaatat tatagcactt     600 tcgtttgtat tttgacaaac attatctaat tatgggactaa ctagatttaa aaaattcgtc     660
tttgtcggcc ttcgcgggcg ccacacgctt catggcaaat tgctccatca tggacatgct     720
cgggaggccg acgactgaag gcggatgtg tggtccatgc gaaggaaggg gacatccaat     780
ccagtgcgaa ggacgagcag tgcagagtga atcggacgg tgacgagaat ggagcatcaa     840
ggctagctcc gatctggctc tagaagaaac accaacctca tatttctttg tgggtctagc     900
tccgggtgta tggatggcca gttagagcct agctctagag gctggtctgg gaaccaaaca     960 atatagggg tgtttgggac tgctctgctc cacgttttc agctccgctc cacgtttttt    1020
agccaaacgg tttcagctcc acgcactcag ttcgagaaaa aagggtggag ttgtgagagc    1080
acctaaagag ttactccacg aactctagtt ttttgtggag ctgctccacg gcggagttta    1140
tggagcagag ttcgtggagc agttccaaac accctcataa atctggccca accaaaccca    1200
aagccagctt ggccagtctt ggagaggcat gggccaccat cgaacgggta ggatcaactg    1260
tcagcgtaag gctaccaagg agatcctcgg ataaaccact ttgacgcctc aataatggtg    1320
tgcagttgtc aaataaatgt gtttattaga cgaaccgatg tagctgagat cagctggtgc    1380
atcctggttt aagtctgagt taaacgtgag tgctcgtatt tttctgcatt tatttcatgg    1440
tttaacgata ttgttttttt gttgttgtag gtgaagtgta tatcaacaac gatatgtttg    1500
tgatgtttgt caatctcaag agatgtcgtg ctcctggtta gtaccagtcc ttcaaaatat    1560
cctcatagga ataagatgtg cacgtgttta taagatgggt gtatgtaca tgtataagtg     1620 tgtgtattat tatactatga ttggcaaaga aaagaagaa gaaatgcgct tagtgcaaat    1680
ttgttcgtgg acatactttc atcacctgcg gtatttgcat atggataaca gttaattttg    1740
```

```
tctttgccca taagtatcct ttaaatgtta taattttcta cccatccata aaatcatgat    1800
ttcctagtat ggatgagaca taactactcg taaaagacaa aattgatact gtgggcctaa    1860
gctggtgagc tatatcttct tcgactcttc gttctttttt cattggaact tgctccgaag    1920
cgtcttgacc ttttgctccc attgtcattc tccaccaccg cccatactcc tagctcactc    1980
ttgagcatca ccaccattgc catggctcgc tgctgctaag gtagcactgg tcgtattcat    2040
cagtcaaagc ggcacttcgc tgagctgaga tagagaagat gacacggtct tgctaccaca    2100
aaaaagagga caccttctc cttatgcaca tgaaaccatc acggtgaggt cctctagtct     2160
tgctagcgcc actaggttga tgaggtgcag aaacgatctt ctatgacaca atggcatcta    2220
gaactggctc gctagtggca gtgctcgtga agtggaggaa caaatagaag cttgaggaag    2280
tgtcgatgca cgatgaggag caaaaattgt ccatgataat tgtgcatgtt tttatttgct    2340
ctcttggaga aataaactac taggtttaca ttttagctat ttttctagct cttgctacaa    2400
tgttactttc acccttcgtg aaaaaaatca cttgagatat tttgattaga atctgtattt    2460
gtatttgtat ttgtatgctc tcttggagta atagtgtagt atgcttgata tgtaagcaaa    2520
ccaaaaaaag agtcaatttc ggcaaccaat ttggggatgt tgcagtccag aaatggaaga    2580
aaaagggcag agcactcacg gacatgcggt cccacatccg tgtggaccca tcagccagtc    2640
cccctgaagc tacccacgt gtcacttgcc acctcgctcc cttgtgcccg acaggcacag     2700
ggtcagggaa aaccatttct caccgcggat ccgcgctacc cacagccgca ccctttccgg    2760
cccacgacgg gctcgaccaa tccctgcccc gcgcgccctg acgagcgcag cactccacg    2820 ccggcctcgc tgggcccatc cttctggccc ataataacga tccccctcgg gatccgacgg    2880
tccatctgcc tccacgccgc tccgaaacct catcgtccaa tcaaaacacg acagcgggtc    2940
aggcaaaacc accgtggttt cgcgataccg ctctcctccc catctaaaac cgcccacctc    3000
```